(12) United States Patent
Bhimavarapu et al.

(10) Patent No.: US 11,710,556 B2
(45) Date of Patent: *Jul. 25, 2023

(54) ACCESS SYSTEMS FOR USE WITH PATIENT SUPPORT APPARATUSES

(71) Applicant: Stryker Corporation, Kalamazoo, MI (US)

(72) Inventors: Krishna S. Bhimavarapu, Kalamazoo, MI (US); Daniel V. Brosnan, Kalamazoo, MI (US); Aaron Douglas Furman, Kalamazoo, MI (US); Alexey Titov, Redmond, WA (US); Michael Hayes, South Haven, MI (US)

(73) Assignee: Stryker Corporation, Kalamazoo, MI (US)

(*) Notice: Subject to any disclaimer, the term of this patent is extended or adjusted under 35 U.S.C. 154(b) by 368 days.

This patent is subject to a terminal disclaimer.

(21) Appl. No.: 17/020,053

(22) Filed: Sep. 14, 2020

(65) Prior Publication Data

US 2020/0411175 A1 Dec. 31, 2020

Related U.S. Application Data

(62) Division of application No. 16/019,986, filed on Jun. 27, 2018, now Pat. No. 10,811,136.

(Continued)

(51) Int. Cl.
*G06F 21/00* (2013.01)
*G16H 40/20* (2018.01)
(Continued)

(52) U.S. Cl.
CPC .............. *G16H 40/20* (2018.01); *G06F 21/30* (2013.01); *G06Q 10/0639* (2013.01); *G16H 40/63* (2018.01)

(58) Field of Classification Search
None
See application file for complete search history.

(56) References Cited

U.S. PATENT DOCUMENTS

| | | | |
|---|---|---|---|
| 5,113,214 A | 5/1992 | Nagata et al. | |
| 5,276,432 A | 1/1994 | Travis | |

(Continued)

FOREIGN PATENT DOCUMENTS

| | | |
|---|---|---|
| CN | 101789230 A | 7/2010 |
| DE | 19505162 C1 | 3/1996 |

(Continued)

OTHER PUBLICATIONS

AHIMA, "Facial Recognition Enters into Healthcare", Journal of AHIMA, Sep. 4, 2018, https://journal.ahima.org/2018/09/04/facial-recognition-enters-into-healthcare/, 4 pages.

(Continued)

*Primary Examiner* — William J. Goodchild
(74) *Attorney, Agent, or Firm* — Howard & Howard Attorneys PLLC

(57) ABSTRACT

An access system for managing users engaged in providing care to patients. A patient support apparatus is provided and comprises a frame, a patient support surface configured to support the patient, and a powered device having a function. An input system is disposed in communication with the powered device and is configured to receive input data. A user control system is disposed in communication with the input system and comprises an authorization module. The authorization module is configured to access a permission level for a user dictating whether the user has permission to operate the powered device with the input system to perform the function. The authorization module is further configured to determine performance data relating to performance of the user in caring for the patient based on the input data, and (Continued)

to modify the permission level based on the performance data.

13 Claims, 12 Drawing Sheets

Related U.S. Application Data

(60) Provisional application No. 62/525,377, filed on Jun. 27, 2017.

(51) Int. Cl.
*G06Q 10/0639* (2023.01)
*G16H 40/63* (2018.01)
*G06F 21/30* (2013.01)

(56) References Cited

U.S. PATENT DOCUMENTS

| | | |
|---|---|---|
| 5,434,621 A | 7/1995 | Yu |
| 5,640,953 A | 6/1997 | Bishop et al. |
| 5,645,667 A | 7/1997 | Kusen |
| 5,664,270 A | 9/1997 | Bell et al. |
| 5,971,913 A | 10/1999 | Newkirk et al. |
| 6,320,510 B2 | 11/2001 | Menkedick et al. |
| 6,340,977 B1 | 1/2002 | Lui et al. |
| 6,362,725 B1 | 3/2002 | Ulrich et al. |
| 6,702,314 B1 | 3/2004 | Crose |
| 6,876,303 B2 | 4/2005 | Reeder et al. |
| 6,948,592 B2 | 9/2005 | Kavounas |
| 7,154,397 B2 | 12/2006 | Zerhusen et al. |
| 7,296,312 B2 | 11/2007 | Menkedick et al. |
| 7,319,386 B2 | 1/2008 | Collins, Jr. et al. |
| 7,336,187 B2 | 2/2008 | Hubbard, Jr. et al. |
| 7,389,552 B1 | 6/2008 | Reed et al. |
| 7,443,302 B2 | 10/2008 | Reeder et al. |
| 7,472,439 B2 | 1/2009 | Lemire et al. |
| 7,487,562 B2 | 2/2009 | Frondorf et al. |
| 7,490,021 B2 | 2/2009 | Holland et al. |
| 7,570,152 B2 | 8/2009 | Smith et al. |
| 7,690,059 B2 | 4/2010 | Lemire et al. |
| 7,747,644 B1 | 6/2010 | Reihl et al. |
| 7,888,901 B2 | 2/2011 | Larson et al. |
| 7,895,519 B1 | 2/2011 | Allegrezza et al. |
| 7,962,981 B2 | 6/2011 | Lemire et al. |
| 8,069,157 B2 | 11/2011 | Jam |
| 8,117,701 B2 | 2/2012 | Bobey et al. |
| 8,121,856 B2 | 2/2012 | Huster et al. |
| 8,143,846 B2 | 3/2012 | Herman et al. |
| 8,165,908 B2 | 4/2012 | Bolle et al. |
| 8,209,608 B1 | 6/2012 | Linyard et al. |
| 8,266,742 B2 | 9/2012 | Andrienko |
| 8,308,237 B2 | 11/2012 | Kunou |
| 8,319,633 B2 | 11/2012 | Becker et al. |
| 8,334,779 B2 | 12/2012 | Zerhusen et al. |
| 8,341,777 B2 | 1/2013 | Hensley et al. |
| 8,344,860 B2 | 1/2013 | Collins, Jr. et al. |
| 8,410,943 B2 | 4/2013 | Metz et al. |
| 8,413,270 B2 | 4/2013 | Turner et al. |
| 8,413,271 B2 | 4/2013 | Blanchard et al. |
| 8,432,287 B2 | 4/2013 | O'Keefe et al. |
| 8,442,738 B2 | 5/2013 | Patmore |
| 8,464,380 B2 | 6/2013 | Bobey et al. |
| 8,525,682 B2 | 9/2013 | Dixon et al. |
| 8,544,126 B2 | 10/2013 | Elliott et al. |
| 8,552,880 B2 | 10/2013 | Kopp et al. |
| 8,604,917 B2 | 12/2013 | Collins et al. |
| 8,641,301 B2 | 2/2014 | Yang et al. |
| 8,650,682 B2 | 2/2014 | Herman |
| 8,674,839 B2 | 3/2014 | Zerhusen et al. |
| 8,716,941 B2 | 5/2014 | Kim |
| 8,756,078 B2 | 6/2014 | Collins, Jr. et al. |
| 8,768,520 B2 | 7/2014 | Oexman et al. |
| 8,789,102 B2 | 7/2014 | Pickelsimer et al. |
| 8,847,756 B2 | 9/2014 | Tallent et al. |
| 8,868,542 B2 | 10/2014 | Kimball et al. |
| 8,870,812 B2 | 10/2014 | Alberti et al. |
| 8,896,524 B2 | 11/2014 | Birnbaum et al. |
| 8,923,994 B2 | 12/2014 | Laikari et al. |
| 8,924,218 B2 | 12/2014 | Corpier et al. |
| 8,926,535 B2 | 1/2015 | Rawls-Meehan |
| 8,984,685 B2 | 3/2015 | Robertson et al. |
| 9,001,038 B2 | 4/2015 | Kasahara |
| 9,032,510 B2 | 5/2015 | Sampathkumaran et al. |
| 9,038,217 B2 | 5/2015 | Elliot et al. |
| 9,088,282 B2 | 7/2015 | Holenarsipur et al. |
| 9,126,571 B2 | 9/2015 | Lemire et al. |
| 9,138,173 B2 | 9/2015 | Penninger et al. |
| 9,173,792 B2 | 11/2015 | Goffer |
| 9,204,823 B2 | 12/2015 | Derenne et al. |
| 9,220,650 B2 | 12/2015 | Bobey et al. |
| 9,230,421 B2 | 1/2016 | Reeder et al. |
| 9,233,033 B2 | 1/2016 | Valentino et al. |
| 9,259,369 B2 | 2/2016 | Derenne et al. |
| 9,262,876 B2 | 2/2016 | Wood et al. |
| 9,320,664 B2 | 4/2016 | Newkirk et al. |
| 9,342,677 B2 | 5/2016 | Ali et al. |
| 9,381,125 B2 | 7/2016 | Herbst et al. |
| 9,424,699 B2 | 8/2016 | Kusens et al. |
| 9,456,938 B2 | 10/2016 | Blickensderfer et al. |
| 9,463,126 B2 | 10/2016 | Zerhusen et al. |
| 9,466,163 B2 | 10/2016 | Kusens et al. |
| 9,486,084 B2 | 11/2016 | Connell et al. |
| 9,569,591 B2 | 2/2017 | Vanderpohl, III |
| 9,593,833 B2 | 3/2017 | McMannon et al. |
| 9,655,798 B2 | 5/2017 | Zerhusen et al. |
| 9,691,206 B2 | 6/2017 | Kusens et al. |
| 9,774,991 B2 | 9/2017 | Kusens |
| 9,814,410 B2 | 11/2017 | Kostic et al. |
| 9,838,849 B2 | 12/2017 | Kusens |
| 9,844,275 B2 | 12/2017 | Nunn et al. |
| 9,849,051 B2 | 12/2017 | Newkirk et al. |
| 9,858,741 B2 | 1/2018 | Kusens et al. |
| 9,892,310 B2 | 2/2018 | Kusens et al. |
| 9,892,311 B2 | 2/2018 | Kusens et al. |
| 9,916,649 B1 | 3/2018 | Kusens |
| 9,934,427 B2 | 4/2018 | Derenne et al. |
| 9,940,810 B2 | 4/2018 | Derenne et al. |
| 9,984,521 B1 | 5/2018 | Kusens et al. |
| 9,997,001 B2 | 6/2018 | Kusens et al. |
| 9,998,857 B2 | 6/2018 | Kusens |
| 9,999,555 B2 | 6/2018 | Magill et al. |
| 10,004,654 B2 | 6/2018 | Zerhusen et al. |
| 10,013,831 B1 | 7/2018 | Kusens et al. |
| 10,034,979 B2 | 7/2018 | Bechtel et al. |
| 10,052,249 B2 | 8/2018 | Elliott et al. |
| 10,090,068 B2 | 10/2018 | Kusens et al. |
| 10,096,101 B2 | 10/2018 | Kusens |
| 10,098,796 B2 | 10/2018 | Valentino et al. |
| 10,109,179 B2 | 10/2018 | Kusens |
| 10,115,253 B2 | 10/2018 | Kusens et al. |
| 10,115,254 B1 | 10/2018 | Kusens et al. |
| 10,121,299 B2 | 11/2018 | Kusens et al. |
| 10,136,841 B2 | 11/2018 | Alghazi |
| 10,147,184 B2 | 12/2018 | Kusens et al. |
| 10,147,256 B2 | 12/2018 | Kusens et al. |
| 10,172,752 B2 | 1/2019 | Goffer |
| 10,187,755 B2 | 1/2019 | Kusens et al. |
| 10,188,569 B2 | 1/2019 | Elku et al. |
| 10,194,278 B1 | 1/2019 | Kusens |
| 10,198,886 B2 | 2/2019 | Kusens et al. |
| 10,210,378 B2 | 2/2019 | Kusens et al. |
| 10,708,745 B2 | 7/2020 | Gravelle et al. |
| 2002/0000727 A1 | 1/2002 | Rass et al. |
| 2002/0014951 A1 | 2/2002 | Kramer et al. |
| 2003/0183427 A1 | 10/2003 | Tojo et al. |
| 2004/0083394 A1 | 4/2004 | Brebner et al. |
| 2006/0077186 A1 | 4/2006 | Park et al. |
| 2006/0102392 A1 | 5/2006 | Johnson et al. |
| 2007/0163045 A1 | 7/2007 | Becker et al. |
| 2007/0219950 A1 | 9/2007 | Crawford |
| 2008/0141459 A1 | 6/2008 | Hamberg et al. |
| 2008/0172789 A1 | 7/2008 | Elliot et al. |

(56) References Cited

U.S. PATENT DOCUMENTS

| | | |
|---|---|---|
| 2008/0235872 A1 | 10/2008 | Newkirk et al. |
| 2009/0153370 A1 | 6/2009 | Cooper et al. |
| 2010/0039414 A1 | 2/2010 | Bell |
| 2010/0212087 A1 | 8/2010 | Leib et al. |
| 2011/0080421 A1 | 4/2011 | Capener |
| 2011/0162067 A1 | 6/2011 | Shuart et al. |
| 2011/0169653 A1 | 7/2011 | Wang et al. |
| 2011/0277242 A1* | 11/2011 | Dionne ................ A61G 7/0507 5/613 |
| 2012/0023670 A1 | 2/2012 | Zerhusen et al. |
| 2012/0089419 A1 | 4/2012 | Huster et al. |
| 2012/0137436 A1 | 6/2012 | Andrienko |
| 2012/0215360 A1 | 8/2012 | Zerhusen et al. |
| 2012/0239173 A1 | 9/2012 | Laikari et al. |
| 2013/0138452 A1 | 5/2013 | Cork et al. |
| 2013/0142367 A1 | 6/2013 | Berry et al. |
| 2013/0227787 A1 | 9/2013 | Herbst et al. |
| 2013/0238991 A1 | 9/2013 | Jung et al. |
| 2013/0300867 A1 | 11/2013 | Yoder |
| 2013/0318716 A1 | 12/2013 | Vanderpohl, III |
| 2014/0076644 A1 | 3/2014 | Derenne et al. |
| 2014/0188512 A1* | 7/2014 | Parker .................... G16H 10/60 705/3 |
| 2014/0259410 A1 | 9/2014 | Zerhusen et al. |
| 2014/0259414 A1* | 9/2014 | Hayes .................. A61B 5/7275 600/595 |
| 2014/0265181 A1 | 9/2014 | Lambarth et al. |
| 2014/0297327 A1 | 10/2014 | Heil et al. |
| 2014/0313700 A1 | 10/2014 | Connell et al. |
| 2014/0342330 A1 | 11/2014 | Freeman et al. |
| 2015/0002393 A1 | 1/2015 | Cohen et al. |
| 2015/0020151 A1* | 1/2015 | Ramanathan ........... H04L 63/20 726/1 |
| 2015/0060162 A1 | 3/2015 | Goffer |
| 2015/0077534 A1 | 3/2015 | Derenne et al. |
| 2015/0109442 A1 | 4/2015 | Derenne et al. |
| 2015/0154002 A1 | 6/2015 | Weinstein et al. |
| 2015/0250669 A1 | 9/2015 | Elliott et al. |
| 2015/0317068 A1 | 11/2015 | Marka et al. |
| 2016/0006765 A1* | 1/2016 | Shem Tov .............. H04L 63/08 726/1 |
| 2016/0012218 A1 | 1/2016 | Perna et al. |
| 2016/0022039 A1 | 1/2016 | Paul et al. |
| 2016/0038361 A1 | 2/2016 | Bhimavarapu et al. |
| 2016/0045382 A1 | 2/2016 | Goffer |
| 2016/0049028 A1 | 2/2016 | Kusens et al. |
| 2016/0050217 A1 | 2/2016 | Mare et al. |
| 2016/0065909 A1 | 3/2016 | Derenne et al. |
| 2016/0095774 A1 | 4/2016 | Bobey et al. |
| 2016/0098676 A1 | 4/2016 | Kusens et al. |
| 2016/0140307 A1* | 5/2016 | Brosnan ................ G06Q 10/10 600/509 |
| 2016/0180668 A1 | 6/2016 | Kusens et al. |
| 2016/0183864 A1 | 6/2016 | Kusens et al. |
| 2016/0193095 A1 | 7/2016 | Roussy et al. |
| 2016/0199240 A1 | 7/2016 | Newkirk et al. |
| 2016/0247342 A1 | 8/2016 | Kusens et al. |
| 2016/0296396 A1 | 10/2016 | Kolar et al. |
| 2016/0324705 A1 | 11/2016 | Bach Castillo |
| 2016/0338891 A1 | 11/2016 | Agdeppa et al. |
| 2016/0366327 A1 | 12/2016 | Kusens |
| 2016/0367420 A1 | 12/2016 | Zerhusen et al. |
| 2016/0371786 A1 | 12/2016 | Kusens et al. |
| 2016/0373313 A1* | 12/2016 | Giri ....................... H04L 43/091 |
| 2017/0026358 A1* | 1/2017 | Hankins ................ H04L 63/08 |
| 2017/0027789 A1 | 2/2017 | St.John et al. |
| 2017/0049642 A9 | 2/2017 | Valentino et al. |
| 2017/0055113 A1 | 2/2017 | Kusens |
| 2017/0076526 A1 | 3/2017 | Kusens et al. |
| 2017/0094477 A1 | 3/2017 | Kusens et al. |
| 2017/0097800 A1 | 4/2017 | Vanderpohl, III |
| 2017/0098048 A1 | 4/2017 | Brosnan et al. |
| 2017/0109770 A1 | 4/2017 | Kusens et al. |
| 2017/0111770 A1 | 4/2017 | Kusens |
| 2017/0116790 A1 | 4/2017 | Kusens et al. |
| 2017/0124844 A1 | 5/2017 | Huster et al. |
| 2017/0128296 A1 | 5/2017 | Kostic et al. |
| 2017/0143565 A1 | 5/2017 | Childs et al. |
| 2017/0193177 A1 | 7/2017 | Kusens |
| 2017/0193180 A1 | 7/2017 | Kusens et al. |
| 2017/0193279 A1 | 7/2017 | Kusens et al. |
| 2017/0193772 A1 | 7/2017 | Kusens et al. |
| 2017/0195637 A1 | 7/2017 | Kusens et al. |
| 2017/0213445 A1 | 7/2017 | Kusens |
| 2017/0224562 A1 | 8/2017 | Zerhusen et al. |
| 2017/0229009 A1 | 8/2017 | Foster et al. |
| 2017/0259811 A1 | 9/2017 | Coulter et al. |
| 2017/0281440 A1 | 10/2017 | Puvogel et al. |
| 2017/0295181 A1* | 10/2017 | Parimi ................ H04L 63/1433 |
| 2017/0352212 A1 | 12/2017 | Kusens et al. |
| 2018/0017945 A1 | 1/2018 | Sidhu et al. |
| 2018/0039743 A1 | 2/2018 | Dixon et al. |
| 2018/0040091 A1 | 2/2018 | Kusens |
| 2018/0041864 A1 | 2/2018 | Kusens |
| 2018/0055418 A1 | 3/2018 | Kostic et al. |
| 2018/0056985 A1 | 3/2018 | Coulter et al. |
| 2018/0084390 A1 | 3/2018 | Kusens |
| 2018/0096550 A1 | 4/2018 | Kusens et al. |
| 2018/0110445 A1 | 4/2018 | Bhimavarapu et al. |
| 2018/0114053 A1 | 4/2018 | Kusens et al. |
| 2018/0137340 A1 | 5/2018 | Kusens et al. |
| 2018/0151010 A1 | 5/2018 | Kusens et al. |
| 2018/0161225 A1 | 6/2018 | Zerhusen et al. |
| 2018/0167816 A1 | 6/2018 | Kusens et al. |
| 2018/0184984 A1 | 7/2018 | Zerhusen et al. |
| 2018/0189946 A1 | 7/2018 | Kusens et al. |
| 2018/0211464 A1 | 7/2018 | Kusens et al. |
| 2018/0218489 A1 | 8/2018 | Kusens |
| 2018/0232979 A1 | 8/2018 | Kusens et al. |
| 2018/0232980 A1 | 8/2018 | Kusens et al. |
| 2018/0247476 A1 | 8/2018 | Kusens et al. |
| 2018/0250177 A1 | 9/2018 | Magill et al. |
| 2018/0271286 A1 | 9/2018 | Jacobs et al. |
| 2018/0271287 A1 | 9/2018 | Jacobs et al. |
| 2018/0279075 A1 | 9/2018 | Kusens |
| 2018/0293826 A1 | 10/2018 | Kusens et al. |
| 2018/0300977 A1 | 10/2018 | Kusens et al. |
| 2018/0303687 A1 | 10/2018 | Moreno et al. |
| 2018/0369035 A1 | 12/2018 | Bhimavarapu et al. |
| 2018/0369037 A1 | 12/2018 | Desaulniers et al. |
| 2018/0369038 A1 | 12/2018 | Bhimavarapu et al. |
| 2018/0369039 A1 | 12/2018 | Bhimavarapu et al. |
| 2018/0374573 A1 | 12/2018 | Bhimavarapu et al. |
| 2018/0374577 A1 | 12/2018 | Bhimavarapu |
| 2018/0376300 A1 | 12/2018 | Kusens et al. |
| 2019/0006046 A1 | 1/2019 | Kusens et al. |
| 2019/0008708 A1 | 1/2019 | Moreno et al. |
| 2019/0019283 A1 | 1/2019 | Kusens |
| 2019/0024882 A1 | 1/2019 | Jonsson et al. |
| 2019/0043192 A1 | 2/2019 | Kusens et al. |
| 2019/0046373 A1 | 2/2019 | Coulter et al. |
| 2019/0073849 A1 | 3/2019 | Kusens et al. |

FOREIGN PATENT DOCUMENTS

| | | |
|---|---|---|
| DE | 10018560 A1 | 10/2001 |
| DE | 102008011899 A1 | 9/2009 |
| DE | 102010015736 A1 | 10/2010 |
| EP | 0727298 A1 | 8/1996 |
| EP | 0727298 31 | 8/1999 |
| EP | 1146185 A2 | 10/2001 |
| EP | 1146185 A3 | 3/2003 |
| EP | 1146185 81 | 6/2005 |
| EP | 2489341 A2 | 8/2012 |
| EP | 2531159 A2 | 12/2012 |
| EP | 2619724 A2 | 7/2013 |
| EP | 2918255 A1 | 9/2015 |
| JP | 2003140631 A | 5/2003 |
| KR | 20130076922 A | 7/2013 |
| WO | 0101913 A1 | 1/2001 |
| WO | 2006089399 A2 | 8/2006 |
| WO | 2011097569 A2 | 8/2011 |
| WO | 2012040554 A2 | 3/2012 |

(56) References Cited

FOREIGN PATENT DOCUMENTS

| | | |
|---|---|---|
| WO | 2014021873 A1 | 2/2014 |
| WO | 2015148578 A2 | 10/2015 |
| WO | 2015157402 A1 | 10/2015 |
| WO | 2015171365 A1 | 11/2015 |
| WO | 2016025927 A1 | 2/2016 |
| WO | 2016049593 A1 | 3/2016 |
| WO | 2016049593 A4 | 5/2016 |
| WO | 2016123595 A1 | 8/2016 |
| WO | 2016196403 A1 | 12/2016 |
| WO | 2016200556 A1 | 12/2016 |
| WO | 2017027427 A1 | 2/2017 |
| WO | 2017031111 A1 | 2/2017 |
| WO | 2017058991 A1 | 4/2017 |
| WO | 2017061471 A1 | 4/2017 |
| WO | 2017070350 A1 | 4/2017 |
| WO | 2017058991 A4 | 5/2017 |
| WO | 2017070350 A4 | 7/2017 |
| WO | 2017124056 A1 | 7/2017 |
| WO | 2017201513 A1 | 11/2017 |
| WO | 2018026979 A1 | 2/2018 |
| WO | 2018154819 A1 | 8/2018 |
| WO | 2018203476 A1 | 11/2018 |
| WO | 2018216387 A1 | 11/2018 |
| WO | 2018236588 A2 | 12/2018 |
| WO | 2018236588 A3 | 1/2019 |

OTHER PUBLICATIONS

Apple, "Adjust the Brightness on you iPhone, IPad, or IPod Touch", https://support.apple.com/en-us/HT202613, 2018, 2 pages.
Astral Healthcare, "Opthalmology Day Surgery Chair Webpage", Apr. 2018, http://astralhealthcare.com/?product=opthalmology-day-surgery-chair, 6 pages.
Campbell, Mikey, "Apple Expected to Replace Touch ID With Two-Step Facial, Fingerprint Bio-Recognition Tech", Apple Insider, Jan. 21, 2017, http://iphone.appleinsider.com/articles/17/01/21/apple-expected-to-replace-touch-id-with-two-step-facial-fingerprint-bio-recognition-tech, 4 pages.
Chouffani, Reda, "Use of Facial Recognition in Healthcare Improves Hospital Security", Dec. 2018, https://searchhealthit.techtarget.com/tip/Use-of-facial-recognition-in-healthcare-improves-hospital-security, 5 pages.
Dai, Sarah, "Meet Five Chinese Start-Ups Pushing Facial Recognition Technology Into the Mainstream", South China Morning Post, Feb. 20, 2018, https://www.scmp.com/tech/start-ups/article/2133234/meet-five-chinese-start-ups-pushing-facial-recognition-technology, 7 pages.
DOGE Medical, "DOC Classic—DOC Surgery Chairs Webpage", 2014, 2 pages, https://web.archive.org/web/20140214203605/http://www.dogemedical.com/pages/en/products/surgery-chairs/doc-classic.php?lang=EN.
English language abstract and machine-assisted English translation for CN 101789230 extracted from espacenet.com database on Aug. 30, 2018, 31 pages.
English language abstract and machine-assisted English translation for DE 10 2008 011 899 extracted from espacenet.com database on Mar. 20, 2019, 13 pages.
English language abstract and machine-assisted English translation for DE 10 2010 015 736 extracted from espacenet.com database on Mar. 20, 2019, 7 pages.
English language abstract and machine-assisted English translation for JP 2003-140631 extracted from espacenet.com database on Aug. 30, 2018, 19 pages.
English language abstract and machine-assisted English translation for KR 2013-0076922 A extracted from espacenet.com database on Aug. 16, 2018, 8 pages.
English language abstract and machine-assisted English translation for WO 2017/061471 extracted from espacenet.com database on Mar. 25, 2019, 26 pages.
English language abstract and machine-assisted English translation for WO 2018/154819 extracted from espacenet.com database on Mar. 25, 2019, 35 pages.
English language abstract and machine-assisted English translation for WO 2018/203476 extracted from espacenet.com database on Mar. 25, 2019, 37 pages.
English language abstract and machine-assisted English translation for WO 2018/216387 extracted from espacenet.com database on Mar. 25, 2019, 43 pages.
English language abstract for DE 100 18 560 extracted from espacenet.com database on Mar. 20, 2019, 2 pages.
English language abstract for DE 195 05 162 C1 extracted from espacenet.com database on Aug. 16, 2018, 1 page.
English language abstract for EP 0 727 298 A1 extracted from espacenet.com database on Aug. 16, 2018, 1 page.
English language abstract for EP 0 727 298 B1 extracted from espacenet.com database on Aug. 16, 2018, 1 page.
English language abstract for EP 1 146 185 A2 extracted from espacenet.com database on Mar. 20, 2019, 2 pages.
English language abstract for EP 1 146 185 A3 extracted from espacenet.com database on Mar. 20, 2019, 2 pages.
English language abstract for EP 1 146 185 B1 extracted from espacenet.com database on Mar. 20, 2019, 2 pages.
Hall, Stephen, "Nest's 3rd Generation Thermostat Gets Some New Views for its Farsight Feature", 9 to 5 Google, Jun. 14, 2016, https://9to5google.com/2016/06/14/nest-3rd-gen-thermostat-views-farsight/, 4 pages.
Hill-Rom, "Centrelia Smart+Bed Brochure" 2017, 11 pages.
Imore, "How to Use Night Shift on your iPhone or iPad", video also found at https://www.imore.com/night-shift, Nov. 1, 2017, 12 pages.
Nwosu, Kingsley C., "Mobile Facial Recognition System for Patient Indentification in Medical Emergencies for Developing Economies", Journal for the Advancement of Developing Economies, vol. 5, Issue 5, 2016, https://digitalcommons.unl.edu/cgi/viewcontent.cgi?article=1009&context=jade, pp. 62-72.
Recliners.LA "Stellar 550 Large Lift Chair Recliner Webpage", Apr. 2018, https://www.recliners.la/products/ultra-comfort-stellar-550-large-lift-chair, 4 pages.
Stryker Medical, "InTouch Critical Care Bed Operations Manual", Aug. 2014, 125 pages.
Stryker, "InTouch Critical Care Bed Model FL27 (2130/2140) Operations Manual—Optional Pendant Control", 2130-009-001 REV C, Apr. 2008, p. 25.
Supportec-Trade, "Portfolilio Webpage", 2017, https://supportec-trade.nl/en, 2 pages.
U.S. Appl. No. 16/019,973, filed Jun. 27, 2018, 90 pages.
U.S. Appl. No. 16/019,986, filed Jun. 27, 2018, 57 pages.
U.S. Appl. No. 16/020,003, filed Jun. 27, 2018, 37 pages.
U.S. Appl. No. 16/020,052, filed Jun. 27, 2018, 48 pages.
U.S. Appl. No. 16/020,068, filed Jun. 27, 2018, 125 pages.
U.S. Appl. No. 16/020,085, filed Jun. 27, 2018, 67 pages.
U.S. Appl. No. 62/525,359, filed Jun. 27, 2017.
U.S. Appl. No. 62/525,363, filed Jun. 27, 2017.
U.S. Appl. No. 62/525,368, filed Jun. 27, 2017.
U.S. Appl. No. 62/525,373, filed Jun. 27, 2017.
U.S. Appl. No. 62/525,377, filed Jun. 27, 2017.
Youtube, "Memory Seat Escape Video", Nov. 4, 2013, https://www.youtube.com/watch?v=xlghNmAK-7A, 1 page.
Youtube, "Microsoft HoloLens: Partner Spotlight with Stryker Communications Video", Feb. 21, 2017, https://www.youtube.com/watch?v=FTPxUGRGpnA, 3 pages.
Youtube, "Umano Medical Med Surg Bed: The Next Generation of Medical Bed (Canadian Version) Video", Apr. 14, 2015, https://www.bing.com/videos/search?q=umano+ook+snow&&view=detail&mid=2407A16C09D0734591912407A16C09D073459191&rvsmid=FFCD5876C49E791738DFFFCD5876C49E791738DF&FORM=VDRVRV, 1 page.

\* cited by examiner

ACCESS SYSTEMS FOR USE WITH PATIENT SUPPORT APPARATUSES

CROSS-REFERENCE TO RELATED APPLICATIONS

The subject patent application is a divisional of U.S. patent application Ser. No. 16/019,986 filed on Jun. 27, 2018, which claims priority to and all the benefits of U.S. Provisional Patent Application No. 62/525,377 filed on Jun. 27, 2017, the disclosures of each of which are hereby incorporated by reference in their entirety.

TECHNICAL FIELD

The present disclosure relates, generally, to patient support apparatuses and, more specifically, to access systems for use with patient support apparatuses.

BACKGROUND

Patient support apparatuses, such as hospital beds, stretchers, cots, tables, wheelchairs, and chairs are used to help caregivers facilitate care of patients in a health care setting. Conventional patient support apparatuses generally comprise a base and a patient support surface upon which the patient is supported. Often, these patient support apparatuses have one or more powered devices with actuators to perform one or more functions, such as lifting and lowering the patient support surface, articulating one or more deck sections, raising a patient from a slouched position, turning a patient, centering a patient, extending a length or width of the patient support apparatus, and the like. Furthermore, these patient support apparatuses typically employ one or more sensors arranged to detect patient movement, monitor patient vital signs, and the like.

When a caregiver wishes to perform a function, such as operating a powered device that adjusts the patient support surface relative to the base, the caregiver actuates an input device of a user interface, often in the form of a touchscreen or a button on a control panel. In order to ensure that the patient receives proper care, the patient support apparatus may employ a security system to prevent unauthorized access to certain features of the patient support apparatus, such as powered device functions. Here, the security system may require the caregiver to enter a password via the user interface before the powered device function can be performed. The security system may also require that the caregiver possess a token, such as an identification badge, before allowing access to the powered device functions.

Modern medical care facilities often employ different types of caregivers to provide patient care and, thus, the patient support apparatus may be utilized by different types of caregivers. Here, the security system is often configured such that certain caregivers are only permitted to access a limited number of powered device functions. However, depending on the type of security system, unauthorized access to powered device functions can be achieved in a number of different ways. By way of example, a caregiver who is not authorized to access a certain powered device function may achieve access by inputting the password of a different caregiver who is authorized. Similarly, a caregiver who is not authorized to access a powered device function may be able to access the powered device function when a different caregiver, who is authorized, is nearby.

While conventional patient support apparatuses have generally performed well for their intended purpose, there remains a need in the art for a patient support apparatus which overcomes the disadvantages in the prior art, which can be used in such a way to ensure that only authorized users are able to access powered device functions, and which affords caregivers and patients with improved usability and functionality in a number of different operating conditions.

DETAILED DESCRIPTION OF THE EMBODIMENTS

Figure 1:
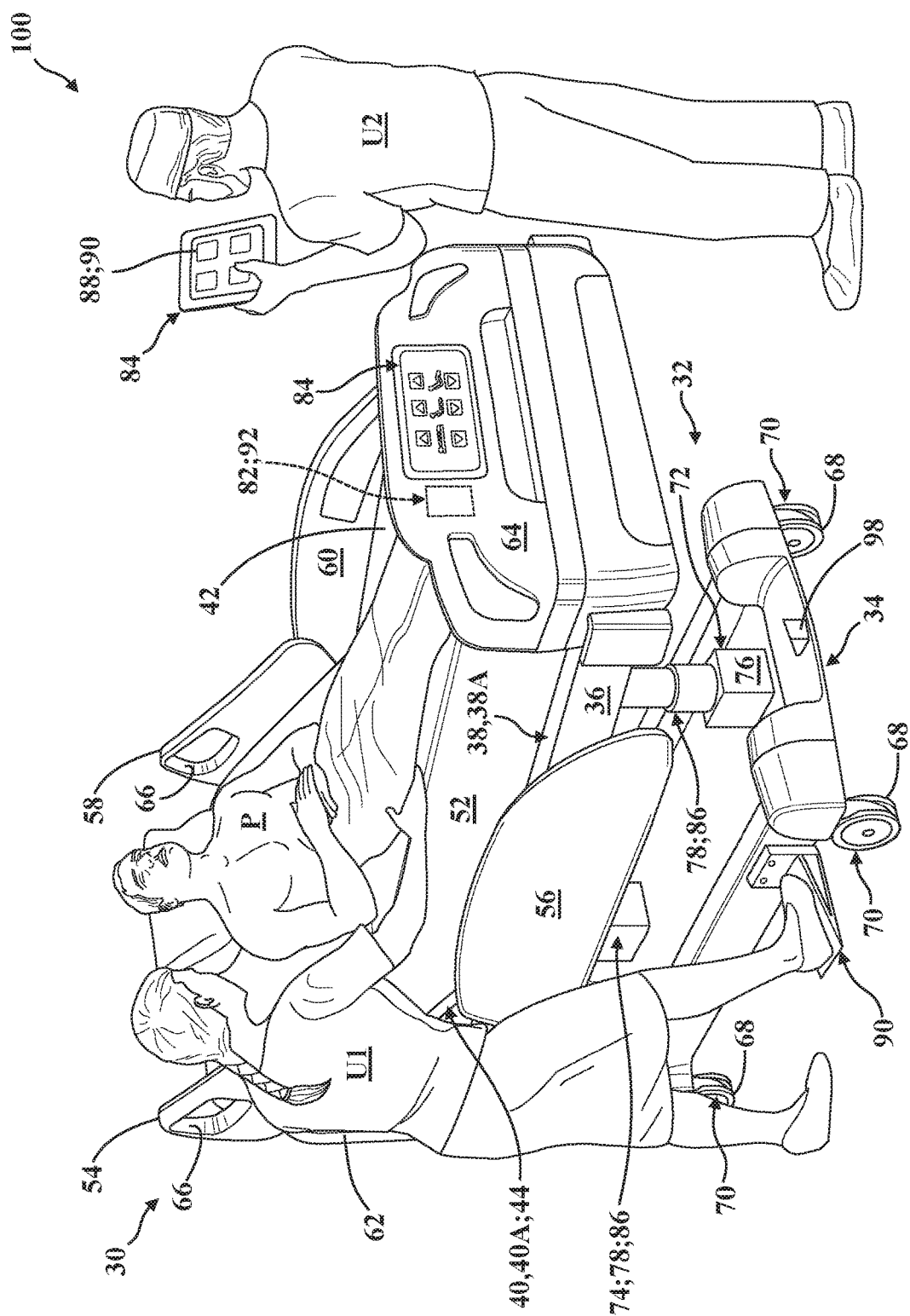
FIG. 1 is a perspective view of a patient support apparatus having powered devices, with two caregivers shown nearby the patient support apparatus.

Referring to FIGS. 1-4, a patient support apparatus 30 is shown for supporting a patient P in a health care setting. The patient support apparatus 30 illustrated throughout the drawings is realized as a hospital bed. In other embodiments, however, the patient support apparatus 30 may be a stretcher, a cot, a table, a wheelchair, a chair, or a similar apparatus utilized in the care of patients P.

A support structure 32 provides support for the patient P. In the representative embodiment illustrated herein, the support structure 32 comprises a base 34, an intermediate frame 36, and a patient support deck 38. The intermediate frame 36 and the patient support deck 38 are spaced above the base 34 in FIGS. 1-2B. As is described in greater detail below, the intermediate frame 36 and the patient support deck 38 are arranged for movement relative to the base 34 between a plurality of vertical configurations 38A, 38B.

The patient support deck 38 has at least one deck section 40 arranged for movement relative to the intermediate frame 36 between a plurality of section positions 40A, 40B. The deck sections 40 of the patient support deck 38 provide a patient support surface 42 upon which the patient P is supported. More specifically, in the representative embodiment of the patient support apparatus 30 illustrated herein, the patient support deck 38 has four deck sections 40 which cooperate to define the patient support surface 42: a back section 44, a seat section 46, a leg section 48, and a foot section 50 (see FIGS. 2A and 2B). Here, the seat section 46 is fixed to the intermediate frame 36 and is not arranged for movement relative thereto. However, it will be appreciated that the seat section 46 could be movable relative to other deck sections 40 in some embodiments. Conversely, the back section 44 and the leg section 48 are arranged for independent movement relative to each other and to the intermediate frame 36, as described in greater detail below, and the foot section 50 is arranged to move partially concurrently with the leg section 48. Other configurations and arrangements are contemplated.

A mattress 52 is disposed on the patient support deck 38 during use. The mattress 52 comprises a secondary patient support surface upon which the patient P is supported. The base 34, the intermediate frame 36, and the patient support deck 38 each have a head end and a foot end corresponding to designated placement of the patient's P head and feet on the patient support apparatus 30. It will be appreciated that the specific configuration of the support structure 32 may take on any known or conventional design, and is not limited to that specifically illustrated and described herein. In addition, the mattress 52 may be omitted in certain embodiments, such that the patient P can rest directly on the patient support surface 42 defined by the deck sections 40 of the patient support deck 38.

Figure 2A:
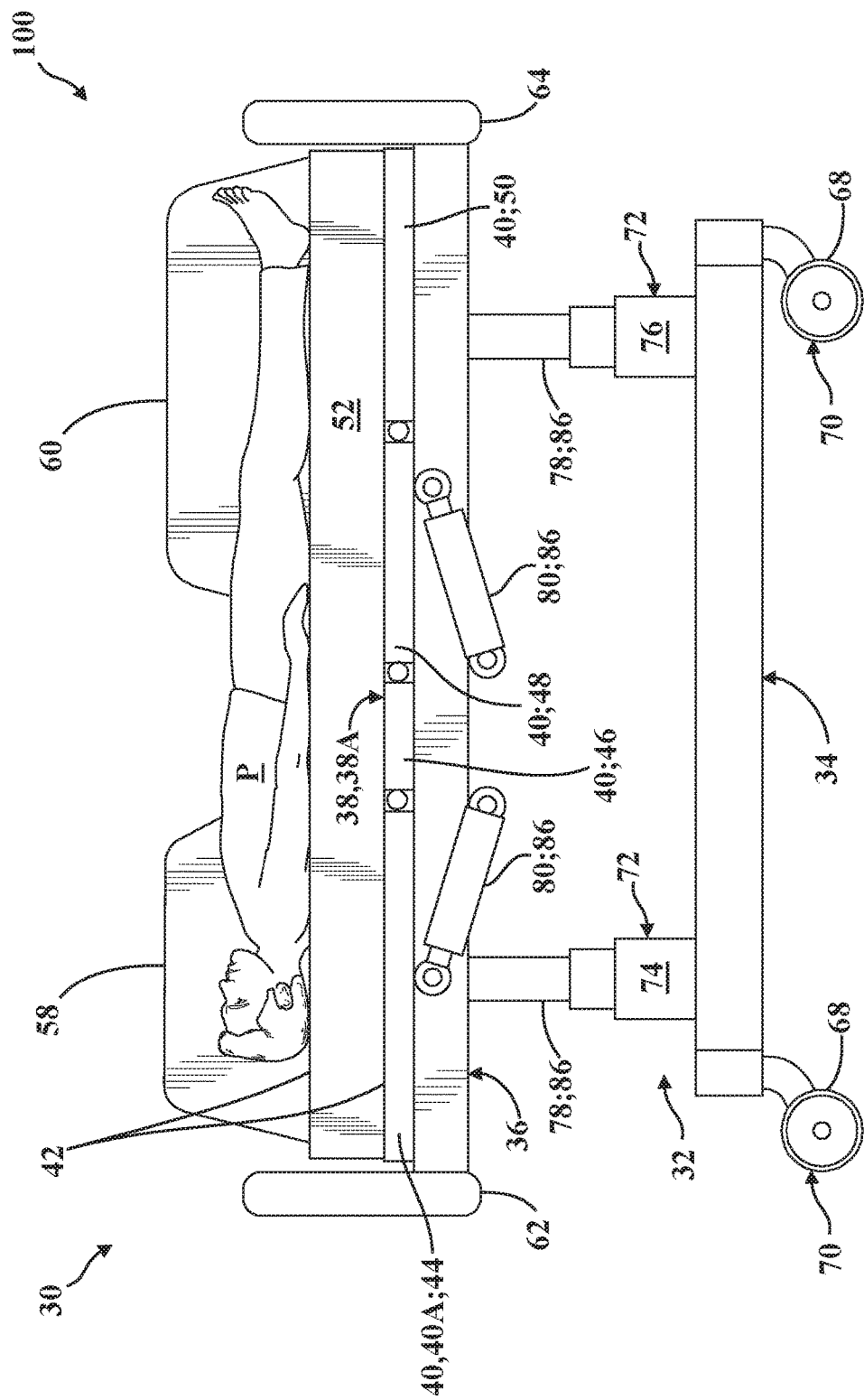
FIG. 2A is a right-side view of a patient support apparatus shown having a patient support deck arranged in a first vertical configuration relative to a base, with a deck section arranged in a first section position.
Figure 2B:
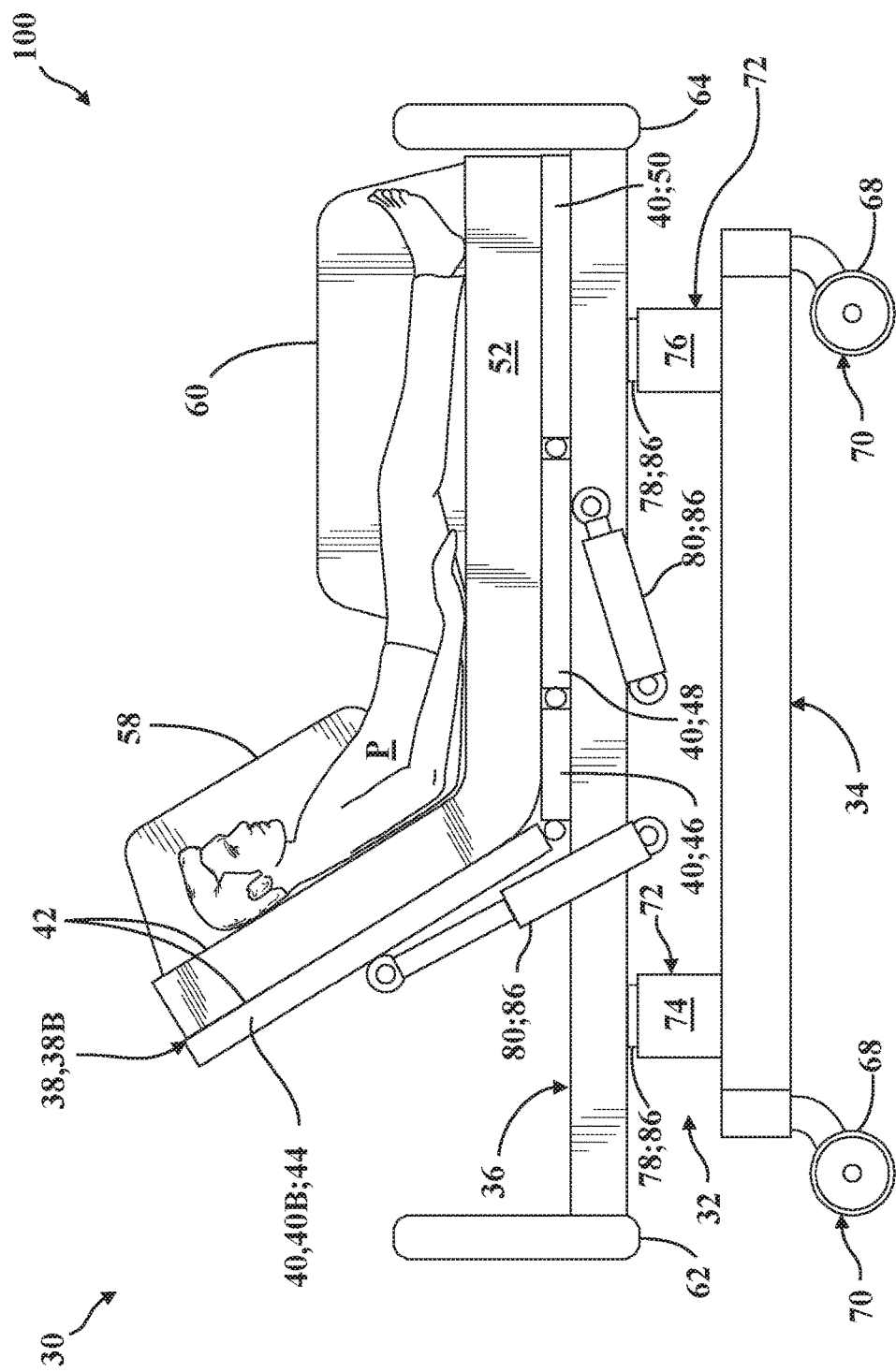
FIG. 2B is another right-side view of the patient support apparatus of FIG. 2A shown with the patient support deck arranged in a second vertical configuration relative to the base, and with the deck section arranged in a second section position.

Side rails 54, 56, 58, 60 are coupled to the support structure 32 and are supported by the base 34. A first side rail 54 is positioned at a right head end of the intermediate frame 36. A second side rail 56 is positioned at a right foot end of the intermediate frame 36. A third side rail 58 is positioned at a left head end of the intermediate frame 36. A fourth side rail 60 is positioned at a left foot end of the intermediate frame 36. The side rails 54, 56, 58, 60 are advantageously movable between a raised position in which they block ingress and egress into and out of the patient support apparatus 30, one or more intermediate positions, and a lowered position in which they are not an obstacle to such ingress and egress. It will be appreciated that there may be fewer side rails for certain embodiments, such as where the patient support apparatus 30 is realized as a stretcher or a cot. Moreover, it will be appreciated that in certain configurations, the patient support apparatus 30 may not include any side rails. Similarly, it will be appreciated that side rails may be attached to any suitable component or structure of the patient support apparatus 30. Furthermore, in certain embodiments the first and third side rails 54, 58 are coupled to a deck section 40 for concurrent movement between section positions 40A, 40B (for example, see FIGS. 2A-2B). In FIGS. 2A-2B, which depict right-side views of the patient support apparatus 30, the first and second side rails 54, 56 are omitted for clarity.

As shown in FIG. 1, a headboard 62 and a footboard 64 are coupled to the intermediate frame 36 of the support structure 32. However, it will be appreciated that the headboard 62 and/or footboard 64 may be coupled to other locations on the patient support apparatus 30, such as the base 34, or may be omitted in certain embodiments.

One or more caregiver interfaces 66, such as handles, are shown in FIG. 1 as being integrated into the first and third side rails 54, 58 to facilitate movement of the patient support apparatus 30 over floor surfaces. Additional caregiver interfaces 66 may be integrated into the headboard 62, the footboard 64, and/or other components of the patient support apparatus 30, such as the second and/or fourth side rails 56, 60, the intermediate frame 36, and the like. The caregiver interfaces 66 are shaped so as to be grasped by a caregiver as a way to position or otherwise manipulate the patient support apparatus 30 for movement. It will be appreciated that the caregiver interfaces 66 could be integrated with or operatively attached to any suitable portion of the patient support apparatus 30, or may be omitted in certain embodiments.

Wheels 68 are coupled to the base 34 to facilitate transportation over floor surfaces. The wheels 68 are arranged in each of four quadrants of the base 34, adjacent to corners of the base 34. In the embodiment shown in FIG. 1, the wheels 68 are caster wheels able to rotate and swivel relative to the support structure 32 during transport. Here, each of the wheels 68 forms part of a caster assembly 70 mounted to the base 34. It should be understood that various configurations of the caster assemblies 70 are contemplated. In addition, in some embodiments, the wheels 68 are not caster wheels. Moreover, it will be appreciated that the wheels 68 may be non-steerable, steerable, non-powered, powered, or combinations thereof. While the representative embodiment of the patient support apparatus 30 illustrated herein employs four wheels 68, additional wheels are also contemplated. For example, the patient support apparatus 30 may comprise four non-powered, non-steerable wheels, along with one or more additional powered wheels. In some cases, the patient support apparatus 30 may not include any wheels. In other embodiments, one or more auxiliary wheels (powered or non-powered), which are movable between stowed positions and deployed positions, may be coupled to the support structure 32. In some cases, when auxiliary wheels are located between caster assemblies 70 and contact the floor surface in the deployed position, they cause two of the caster assemblies 70 to be lifted off the floor surface, thereby shortening a wheel base of the patient support apparatus 30. A fifth wheel may also be arranged substantially in a center of the base 34.

The patient support apparatus 30 further comprises a lift mechanism, generally indicated at 72, which operates to lift and lower the intermediate frame 36 relative to the base 34 which, in turn, moves the patient support deck 38 between a first vertical configuration 38A (for example, a "raised" vertical position as depicted in FIG. 2A), a second vertical configuration 38B (for example, a "lowered" vertical position as depicted in FIG. 2B), or to any desired vertical position in between. To this end, the lift mechanism 72 comprises a head end lift member 74 and a foot end lift member 76 which are each arranged to facilitate movement of the intermediate frame 36 with respect to the base 34 using one or more lift actuators 78 (see FIGS. 2A-3; not shown in detail). The lift actuators 78 may be realized as linear actuators, rotary actuators, or other types of actuators, and may be electrically operated and/or may be hydraulic. It is contemplated that, in some embodiments, only one lift member and one associated lift actuator may be employed, e.g., to raise only one end of the intermediate frame 36, or one central lift actuator to raise and lower the intermediate frame 36. The construction of the lift mechanism 72, the head end lift member 74, and/or the foot end lift member 76 may take on any known or conventional design, and is not limited to that specifically illustrated. By way of non-limiting example, the lift mechanism 72 could comprise a "scissor" linkage arranged between the base 34 and the intermediate frame 36 with one or more actuators configured to facilitate vertical movement of the patient support deck 38.

As noted above, the patient support deck 38 is operatively attached to the intermediate frame 36, and the deck section 40 is arranged for movement between a first section position 40A (see FIG. 2A) and a second section position 40B (see FIG. 2B). To this end, one or more deck actuators 80 are interposed between the deck section 40 and the intermediate frame 36 to move the deck section 40 between the first section position 40A (see FIG. 2A), the second section position 40B (see FIG. 2B), and any other suitable section position. In the representative embodiment illustrated herein, the deck actuator 80 is realized as a linear actuator disposed in force-translating relationship between the deck section 40 and the intermediate frame 36. More specifically, one deck actuator 80 is provided between the intermediate frame 36 and the back section 44, and another deck actuator 80 is provided between the intermediate frame 36 and the leg section 48, and each of the deck actuators 80 is arranged for independent movement to position the respective deck sections 40 to adjust the shape of the patient support surface 42 between a plurality of patient support configurations (for example, a flat configuration, a raised fowler configuration, a seated configuration, etc.).

Those having ordinary skill in the art will appreciate that the patient support apparatus 30 could employ any suitable number of deck actuators 80, of any suitable type or configuration sufficient to effect selective movement of the deck section 40 relative to the support structure 32. By way of non-limiting example, the deck actuator 80 could be a linear actuator or one or more rotary actuators driven electronically and/or hydraulically, and/or controlled or driven in any suitable way. Moreover, the deck actuator 80 could be mounted, secured, coupled, or otherwise operatively attached to the intermediate frame 36 and to the deck section 40, either directly or indirectly, in any suitable way. In addition, one or more of the deck actuators 80 could be omitted for certain applications.

Figure 3:
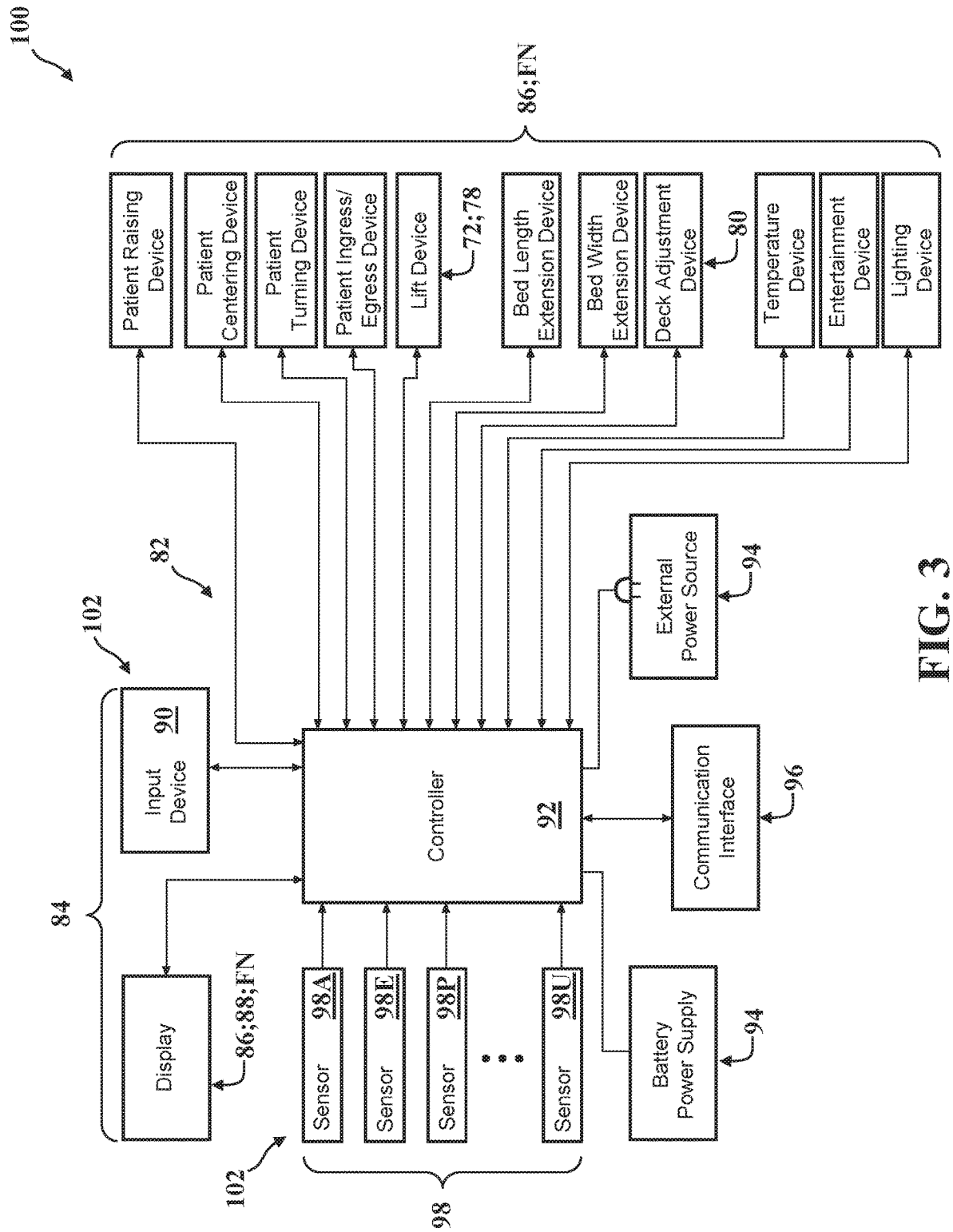
FIG. 3 is a schematic view of a control system of the patient support apparatus of FIGS. 1-2B according to one embodiment.

As shown in FIG. 3, the patient support apparatus 30 employs a control system, generally indicated at 82, to effect operation of various functions of the patient support apparatus 30, as described in greater detail below. To this end, the control system 82 comprises one or more user interfaces, generally indicated at 84, disposed in communication with various powered devices, generally indicated at 86, which are configured to perform respective functions FN. Here, a user U (for example, a caregiver) can carry out functions FN of the various powered devices 86 of the patient support apparatus 30 via the user interface 84.

In the representative embodiment which is depicted schematically in FIG. 3, the user interface 84 comprises a display 88 and an input device 90 which are each disposed in communication with a controller 92. Here, the controller 92 drives the powered devices 86 to carry out the functions FN of the patient support apparatus 30 in response to actuation of the input device 90. In this embodiment, input device 90 is realized as a touchscreen which receives tactile input from the user U and which cooperates with the display 88 to facilitate navigation of visual content presented on the display 88, such as a graphical user interface (GUI). However, as will be appreciated from the subsequent description below, the patient support apparatus 30 could be provided with any suitable number of user interfaces 84, of any suitable type or configuration sufficient to be selectively actuated by the user U to drive powered devices 86. For example, the user interface 84 could comprise one or more input devices 90 realized as discrete buttons or switches. Other types of user interfaces 84 are contemplated herein, such as those utilizing vocal-based activation, gesture-based activation, and the like.

With continued reference to FIG. 3, in some embodiments, the control system 82 of the patient support apparatus 30 comprises a power supply 94, such as an on-board battery and/or an external power supply, configured to provide electrical power to the patient support apparatus 30 to facilitate operation of the powered devices 86. The control system 82 may further comprise a communication interface 96 to facilitate interaction between different patient support apparatuses 30 as well as other user interfaces 84, powered devices 86, systems, and components external to the patient support apparatus 30, as described in greater detail below. Here, the communication interface 96 could be of any suitable type or configuration to facilitate electronic communication, such as via a wired connection (for example, a wired Ethernet connection to a local area network) or a wireless connection (for example, Wi-Fi, Bluetooth, Near Field Communication (NFC), Radio-Frequency Identification (RFID) and the like). Other types of communication interfaces 96 are contemplated.

In some embodiments, sensors 98 are provided to determine, detect, record, sense, or otherwise observe changes in connection with the patient support apparatus 30, the user U, and/or the patient P. By way of example, the patient support apparatus 30 may comprise one or more apparatus sensors, generally indicated at 98A, which are configured to determine changes in or relating to the position, operation, status, and the like, of one or more components or systems of the patient support apparatus 30. For example, apparatus sensors 98A could be provided to determine movement of the patient support deck 38 between the vertical configurations 38A, 38B, as noted above. In some embodiments, environment sensors 98E may also be provided to determine changes in the environment surrounding the patient support apparatus 30, such as ambient lighting, temperature, humidity, noise, or any other quantifiable environmental variable. Furthermore, patient sensors 98P are provided in some embodiments to determine changes in the patient's P status, condition, health, and the like. By way of non-limiting example, patient sensors 98P could detect changes in the patient's heart rate, blood pressure, breathing rate, temperature, position on the patient support deck 38, or any other quantifiable variable associated with the patient. Similarly, in some embodiments, user sensors 98U are provided to determine changes in the user's status, condition, health, performance, and the like. The sensors 98A, 98E, 98P, 98U will be described in greater detail below.

As noted above, the control system 82 of the patient support apparatus 30 is configured to facilitate operation of one or more powered devices 86 to carry out various functions FN. Here, those having ordinary skill in the art will appreciate that the patient support apparatus 30 may comprise a number of different powered devices 86 to carry out different functions FN. By way of non-limiting illustration, powered devices 86 may comprise patient raising devices, patient centering devices, patient turning devices, patient ingress/egress devices, lift devices (for example, lift actuators 78), bed length extension devices, bed width extension devices, deck adjustment devices (for example, deck actuators 80), temperature devices (for example, heated mattresses 52), entertainment devices (for example, television displays or screens), lighting devices, or any other type of powered device 86 suitable for use in connection with patient support apparatuses 30. Furthermore, it will be appreciated that a single powered device 86 may comprise a number of different components, actuators, sensors, and the like, and may carry out different functions FN. By way of non-limiting example, powered devices 86 realized as lift devices may comprise two lift actuators 78 which cooperate to carry out the function FN of raising/lowering the patient support deck 38 relative to the base 34, and which are independently operable to carry out the function FN of "tilting" the patient support deck 38 relative to the base 34 (for example, to place the patient P in the Trendelenburg position). While the various user interfaces 84 and powered devices 86 noted above are generally formed integrally with or otherwise as a part of the patient support apparatus 30 itself, it will be appreciated that one or more user interfaces 84 and/or powered devices 86 could be provided external to or separate from the patient support apparatus 30 to carry out various functions FN, such as a powered device 86 realized as an electronic lock without a discrete user interface 84. Other configurations are contemplated.

Figure 4:
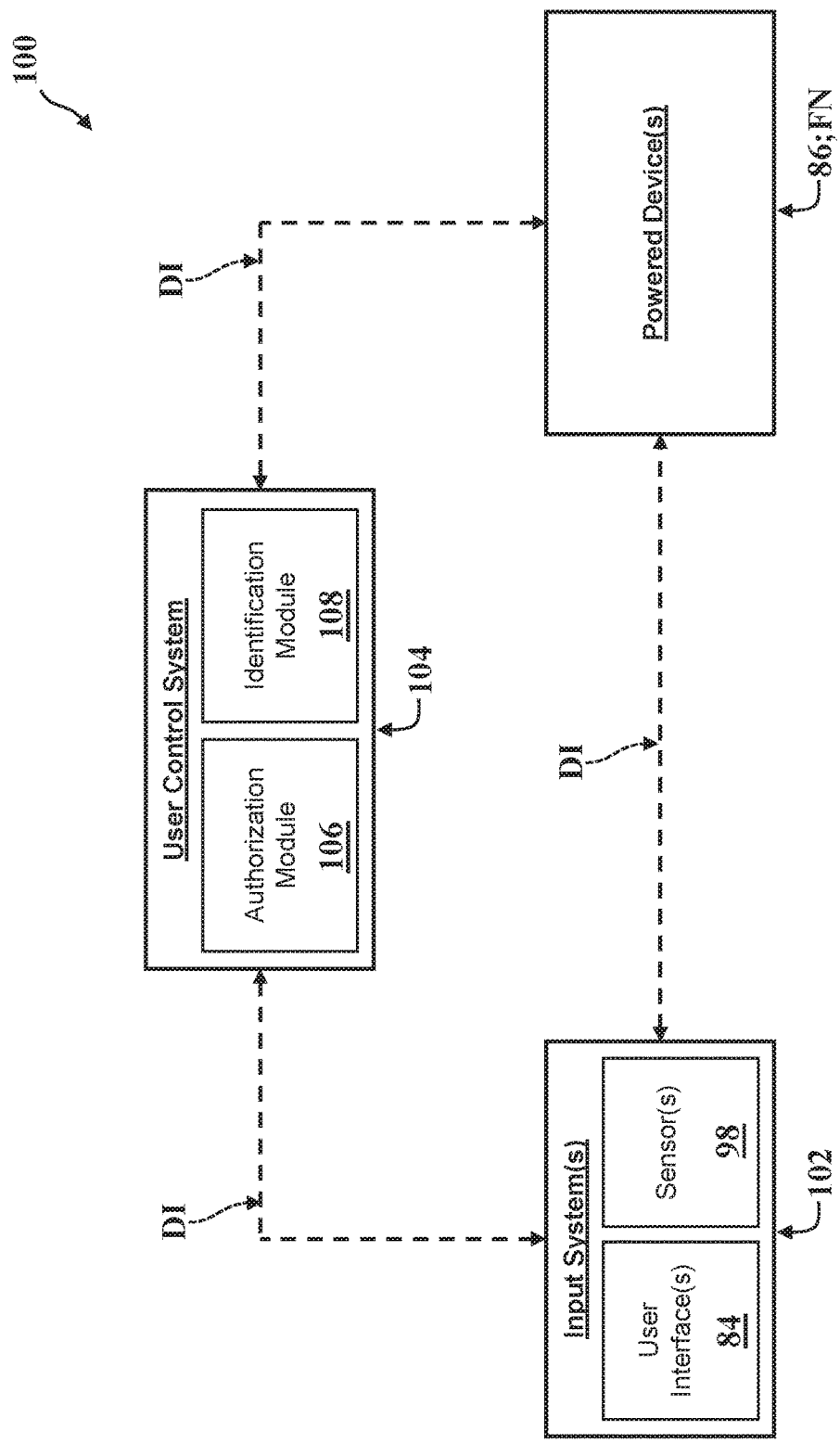
FIG. 4 is a schematic view of a patient support system comprising an input system, a powered device, and a user control system with an authorization module and an identification module according to one embodiment.
Figure 5:
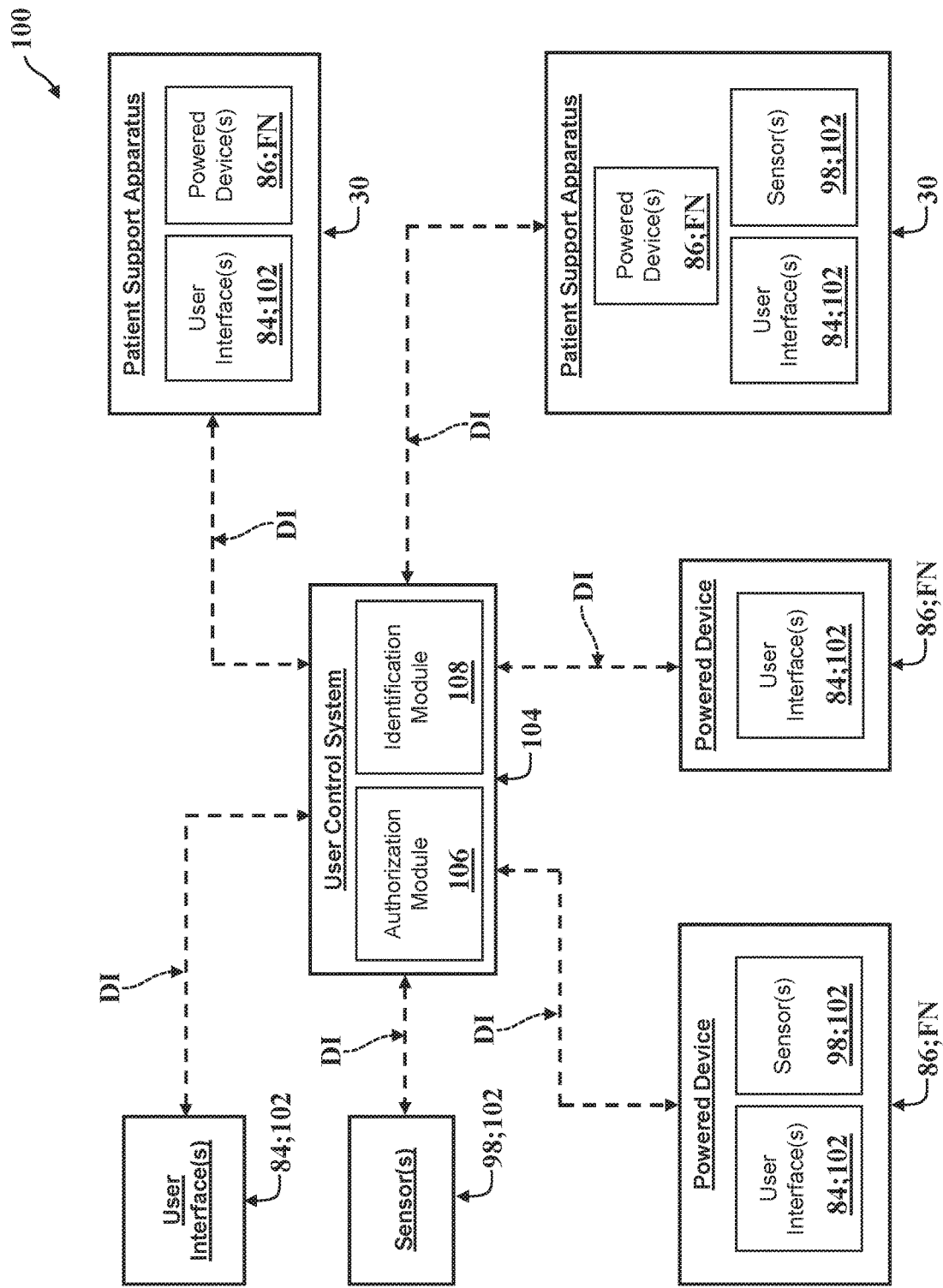
FIG. 5 is a schematic view of another patient support system.
Figure 6:
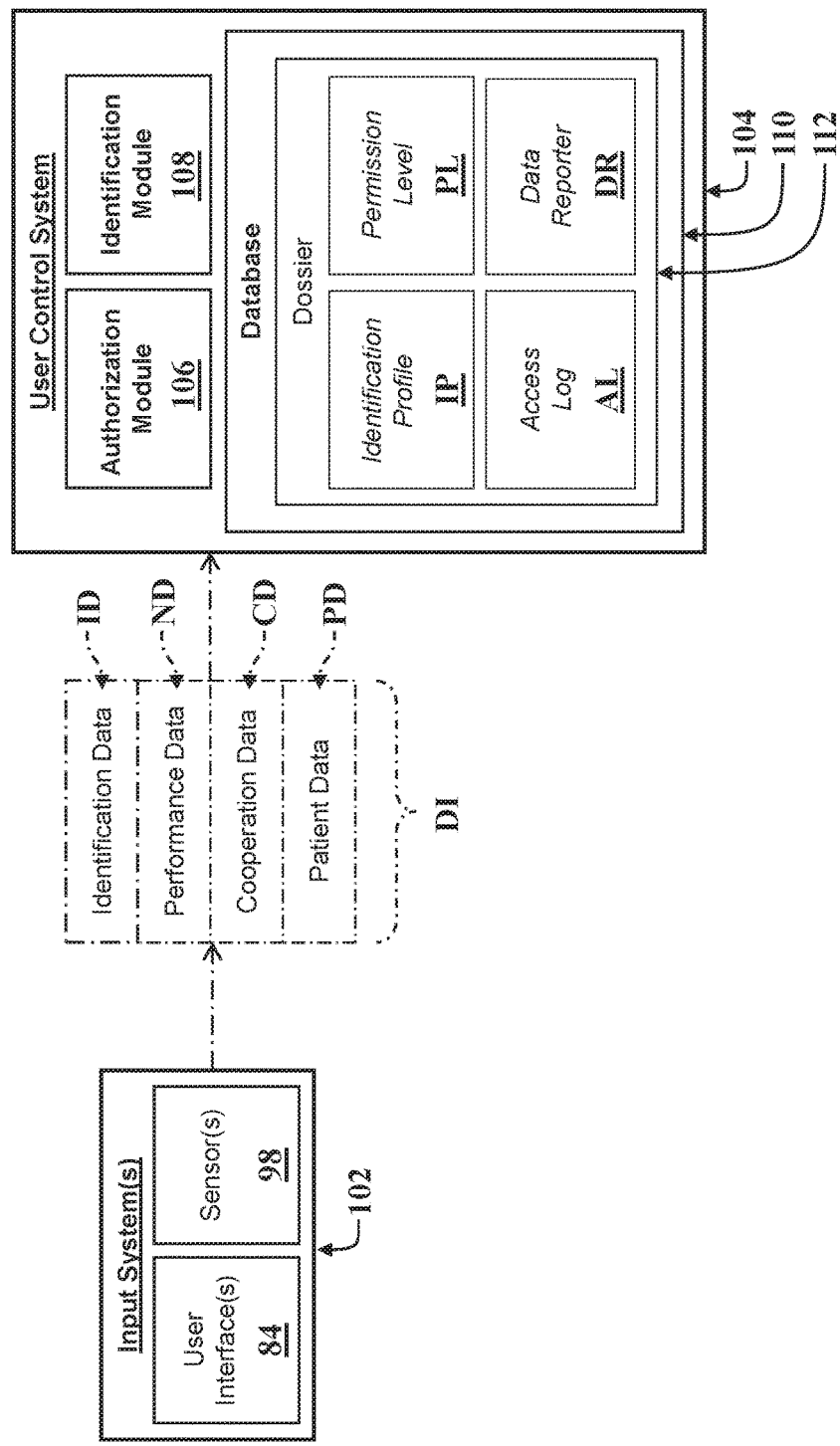
FIG. 6 is an illustrative view of a patient support system depicting data communicated from an input system to a user control system.

Referring now to FIGS. 1-6, an access system for managing users U engaged in providing care to patients P is generally shown at 100. As is best shown in FIG. 4, the access system 100 generally comprises an input system 102, a user control system 104, and a powered device 86. As is described in greater detail below, the input system 102 is configured to receive input data DI from one or more user interfaces 84 and/or sensors 98, and the user control system 104 uses these input data DI to, among other things: identify users U; monitor user U performance; monitor cooperation between multiple users U; and monitor patients P. Here, as is depicted in FIG. 6, input data DI may comprise identification data ID, performance data ND, cooperation data CD, and/or patient data PD, each of which will be described in greater detail below. Communication between the input system 102, the user control system 104, and/or the powered device 86 allows the access system 100 to identify and respond to certain changes in input data DI to, among other things: prevent unauthorized users U from accessing powered device 86 functions FN; prevent otherwise authorized users U from accessing powered device 86 functions FN in certain situations; allow otherwise unauthorized users U to access powered device 86 functions FN in certain situations; identify, track, and respond to changes in user U behavior, health, physiology, status, condition, performance, habits, age, and the like; identify, track, and respond to changes in patient P behavior, health, physiology, status, condition, and the like; and/or correlate changes in input data DI associated with users U with changes in input data DI associated with patients P. As will be appreciated from the subsequent description below, the term "respond" as used herein may be defined or otherwise implemented in a number of different ways depending on the specific configuration of the access system 100. By way of non-limiting example, the access system 100 may "respond" to changes in input data DI by updating identification data ID and/or by changing a user's U ability to access powered device 86 functions 86, as is described in greater detail below.

As noted above, the input system 102 is disposed in communication with the powered device 86 and is configured to receive or otherwise generate input data DI. To this end, the input system 102 may comprise one or more user interfaces 84 and/or one or more sensors 98. By way of illustration, a user U may actuate an input device 90 (for example, a button) of a user interface 84 to request access to a powered device 86 function FN, or a sensor 98 may sense a user's U proximity to the powered device 86, and may collect input data DI such as biometric identification data ID to ensure that the user U is authorized to access the powered device 86 function FN. Those having ordinary skill in the art will appreciate that the input system 102 could comprise both user interfaces 84 and sensors 98 in certain embodiments. Moreover, the user interface 84 itself may rely on one or more sensors 98 to collect input data DI and, thus, a single sensor 98 could collect different types of input data DI. By way of illustration, user interfaces 84 realized as touchscreens could employ touch sensors 98 configured to collect input data DI generated from what the user U inputs on the touchscreen (for example, a multi-character passcode typed on a virtual keyboard), as well as input data DI generated by how the user U engages the touchscreen (for example, the characteristic pattern, speed, force, and the like with which the user U inputs the passcode characters).

Continuing with this illustration, a user's U passcode could be the characters 123ABC and the user U may habitually enter the characters 1, 2, and 3 in quick succession, pause, and then enter the characters A, B, and C more slowly (for example, 1-2-3-A-B-C). Thus, in this embodiment, input data DI concern the specific passcode entered by the user U, and other input data DI (such as identification data ID) concern how the passcode is entered by the user U, and all input data DI can be checked before access to the powered device 86 function FN is allowed. Thus, even if a different user were to obtain the user's passcode (123ABC), the access system could be configured to differentiate how that passcode is entered by different users U and could prevent unauthorized access to the powered device 86 function FN. It will be appreciated that the forgoing illustration is exemplary and non-limiting.

As noted above, the access system 100 could be configured to receive certain kinds of input data DI from user interfaces 84 which are not associated with patient support apparatuses 30 or powered devices 86. For example, the user interface 84 could comprise a portable electronic device, such as a mobile phone, computer, tablet, and the like, which is carried and utilized by the user U. Here, input data DI from the portable electronic device could be communicated to the access system 100 to monitor the user U (for example, with motion or location data), and also to authenticate the user's U presence (for example, using the portable electronic device as a token/badge registered with the communication interface 96, such as via Near Field Communication or other types of wireless communication). Thus, it will be appreciated that portable electronic devices, such as the user's U personal mobile phone, can serve as part of, or otherwise cooperate with, the access system 100.

As noted above, the input data DI received and/or generated by the input system 102 could comprise a number of different types, including without limitation: user keystroke data, user touchscreen data, user movement data, user physiological data, user sound data, and/or user biometric data; as well as patient age data, patient condition data, patient physiological data, and/or patient treatment data. Here too, the input data DI could comprise an electronic medical record (EMR).

As noted above, input data DI could be received or generated by the input system 102 from different types of sensors 98. Here, sensors 98 can be configured so as to be responsive to changes in any measurable variable. By way of non-limiting example, the input system 102 could comprise apparatus sensors 98A configured to measure changes in or relating to the position, status, and/or configuration of various components of the patient support apparatus 30, such as with potentiometers, load cells, accelerometers, gyroscopes, hall-effect sensors, limit switches, and the like.

Further, the input system 102 could comprise environment sensors 98E configured to measure changes in the environment adjacent to the patient support apparatus 30, such as with thermocouples or thermistors, humidity or moisture sensors, light sensors, microphones or noise sensors, location or positioning sensors, smoke or particulate sensors, odor or smell sensors, and the like. Further still, the input system 102 could comprise patient sensors 98P configured to measure changes associated with the patient's P condition, health, vital signs, position, status, and the like, such as with cardiac or heartrate sensors, breathing sensors, body temperature sensors, fluid or hydration sensors, blood oxygen sensors, weight distribution sensors, movement sensors, visual sensors such as cameras, blood pressure sensors, perspiration sensors, and the like. Similarly, the input system 102 could comprise user sensors 98U configured to measure changes associated with the user's U condition, health, performance, vital signs, sobriety, and the like, with similar or different sensors 98 as the patient sensors 98P noted above.

Moreover, it is conceivable that user sensors 98U, the patient sensors 98P, or any other sensors 98, could be configured to track, monitor, and/or identify the user U, the patient P, or any other person based on biometric information. By way of non-limiting example, sensors 98 could be used to identify, track, and/or differentiate between users U and/or patients P based on one or more of the following: patterns in walking/gait, heartrate, breathing, typing; fingerprints; iris scans; visual facial recognition; vocal/speaking cadence, pitch, tone, volume, accent; overall height, width, weight; body/build type; muscle tone; odor, smell, fragrance; color of skin, hair, eyes; presence, type, arrangement of hair on, head, face, body; and gender. Other types of sensors 98, user interfaces 84, and/or input systems 102 are contemplated.

It will be appreciated that the input system 102 could be comprised of any suitable combination of user interfaces 84 and/or sensors 98, located or arranged in any suitable way sufficient to receive and/or generate input data DI communicated to the user control system 104 and/or the powered device 86. By way of non-limiting example, and as is depicted in the embodiment illustrated schematically in FIG. 5, the input system 102 could comprise one or more of: sensors 98 and/or user interfaces 84 coupled to the patient support apparatus 30; sensors 98 and/or user interfaces 84 spaced from the patient support apparatus 30; and sensors 98 and/or user interfaces 84 coupled to powered devices 86 formed separately from the patient support apparatus 30. Similarly, it will be appreciated that the access system 100 can comprise different arrangements and configurations of input systems 102, user control systems 104, and/or powered devices 86 which cooperate to facilitate management of users U engaged in providing care to patients P.

With continued reference to FIG. 5, for example, one patient support apparatus 30 could comprise one or more user interfaces 84 and one or more powered devices 86; and another patient support apparatus 30 could comprise one or more user interfaces 84, one or more powered devices 86, and also one or more sensors 98. Thus, patient support apparatuses 30 used in connection with the access system 100 could serve different purposes, could have different configurations, and could utilize different powered devices 86 (for example, one could be a hospital bed with powered lift mechanism, and the other could be a motorized wheelchair). In some embodiments, the access system 100 is configured to "automatically authenticate" the user U to facilitate seamlessly transitioning between different patient support apparatuses 30, powered devices 86, and/or user interfaces 84 without necessitating that the user U be "re-authenticated" each time they interact with a device, system, interface, and the like, of the the access system 100.

It will be appreciated that the access system 100 described herein can also be used in connection with powered devices 86 which are remote from the patient support apparatus 30. Put differently, certain powered devices 86 in communication with the access system 100 do not necessarily form a part of any patient support apparatus 30. By way of non-limiting example, powered devices 86 could be realized as powered tools, instrumentation, terminals, communication systems, alarm and/or security systems, tracking systems, electronic locks, or any other suitable type of powered device 86 used in connection with providing care to patients P. As depicted in FIG. 5, powered devices 86 can be configured in different ways, can employ dedicated user interfaces 84, and can be implemented with or without discrete sensors 98. Furthermore, it will be appreciated that the access system 100 could comprise user interfaces 84 and/or sensors 98 that are separate from any of the patient support apparatuses 30 and/or powered devices 86. By way of non-limiting example, wall-mounted sensors 98, such as cameras, could be provided for monitoring users U. Other arrangements of the input system 102 are contemplated.

Referring now to FIGS. 4-6, as noted above, the user control system 104 communicates between the input system 102 and the powered devices 86 to manage users U engaged in providing care to patients P. To this end, in some embodiments, the user control system 104 comprises an authorization module, depicted schematically at 106. The authorization module 106 is configured to access a permission level PL for a user U dictating whether that user U has permission to operate certain powered devices 86 with the input system 102 to perform the function FN. The authorization module 106 is further configured to determine performance data ND relating to performance of individual users U in caring for patients P based on the input data DI from the input system 102, and the authorization module can modify the user's U permission level PL based on the performance data ND. As is described in greater detail below, the authorization module 106 can allow, limit, or otherwise prevent users U from accessing one or more functions FN of one or more powered devices 86 of the access system 100 based on the user's performance, as communicated via performance data ND that are received, generated, or determined via the input system 102. In one embodiment, if the user U makes too many mistakes, such as based performance data ND failing to meet certain predetermined thresholds, that user U may be locked out of or otherwise prevented from operating powered devices 86 with the input system 102 to perform functions FN.

Those having ordinary skill in the art will appreciate that operation of the authorization module 106 requires that the access system 100 be configured to identify and differentiate between users U. In some embodiments, the operation of the authorization module 106 described herein can be based on conventional user U identification and differentiation methods or systems, such as passcodes, identification badges, and the like. However, in certain embodiments, the control system 104 of the access system 100 comprises an identification module, indicated schematically at 108, which is configured to identify and differentiate between users U and/or patients P. The identification module 108 is generally configured to access identification profiles IP associated with users U, to receive identification data ID relating to the users U, and to update the respective user U identification profiles IP based on the identification data ID received from the input system 102. Put differently, the identification module 108 is able to review previously observed/recorded identification data ID associated with specific users U, and can update that user's U identification profile IP with newly-observed identification data ID at predetermined frequencies or at predetermined intervals. The authorization module 106, the permission level PL, the identification module, and the identification profiles IP will each be described in greater detail below.

It will be appreciated that the authorization module 106 and/or the identification module 108 of the user control system 104 can be realized in a number of different ways and from a number of different components. By way of non-limiting example, the modules 106, 108 could employ one or more microprocessors for processing instructions or for processing an algorithm stored in memory to control operation of the access system 100, facilitate cooperation between and communication with the powered devices 86 and input system 102, and the like. Additionally or alternatively, the user control system 104 may comprise one or more microcontrollers, field programmable gate arrays, integrated circuits, discrete circuits, and/or any other suitable hardware, software, or firmware that is capable of carrying out the various functions and operations described herein. Furthermore, it will be appreciated that the user control system 104 could be realized as a number of different components and/or systems that can be integrated with or formed separately from the patient support apparatuses 30, the powered devices 86, and/or the input system 102. Specifically, any part of the user control system 104 could be integrated into the patient support apparatus 30 (for example, an on-board processor), or could be located remotely from the patient support apparatus 30 (for example, a server). Other configurations of the control system 104 are contemplated.

In the representative embodiment illustrated in FIG. 6, the user control system 104 comprises a database, depicted schematically at 110, which stores dossiers 112 assigned to respective users U and/or patients P. To this end, the database 110 may be realized as memory (for example, non-volatile memory stored/accessed on a server). In some embodiments, the information stored in the database 110 can be accessed and/or updated by the authorization module 106 and/or the identification module 108, and may be updated with various types of input data DI which are received from, generated by, or otherwise communicated via the input system 102 in connection with users U and/or patients P.

The dossiers 112 may comprise one or more of: stored permission levels PL associated with the ability of the respective user U or patient P to access/perform functions FN via powered devices 86; identification profiles IP associated with stored input data DI, including identification data ID, performance data ND, cooperation data CD, and/or patient data PD; access logs AL associated with the user U or patient's P attempted and/or actual use of powered device 86 functions FN; and data reporters DR configured to facilitate communication of particular situations, trends, and/or changes observed in input data DI. In some embodiments, unauthorized access may be recorded in the access log Al associated with the dossier 112 of the user U. In some embodiments, the information stored in the database 110 and/or dossiers 112 can be accessed, updated, and/or reviewed directly by certain users, such as supervisors who setup new users U, review changes in user U performance data ND, review access logs AL, and the like.

As noted above, in some embodiments, the access system 100 employs the identification module 108 of the user control system 104 to dynamically monitor users U and/or patients P, and to update the user U identification profiles IP in the dossiers 112 based on input data DI received, generated, or determined via the input system 102. In some embodiments, the identification module 108 also uses input data DI to dynamically identify and differentiate users U and/or patients P from each other. It will be appreciated that different types of identification data ID and/or other input data DI can be checked, updated, and/or compared against historical input data DI in the identification profile IP to ensure that users U are properly identified. Here, consistent, reliable identification of users U via the identification module 108 allows the access system 100 to ensure that the authorization module 106 properly controls user U access to powered device 86 functions FN.

The access system 100 can adaptively recognize, monitor, and/or update user U identification profiles IP based on fluctuations over different times of the day, different days of the week, different months of the year, and the like. By way of illustration, different users U may utilize or otherwise interact with the access system 100 according to different schedules, based such as on a shift schedule or hospital rounds. Thus, it will be appreciated that the access system 100 can be configured to recognize access requests or habits which occur at unusual times and can respond by performing additional checks against the user's U identification profile IP, by flagging the user U for further review without modifying the user's U permission level PL, by restricting the user's permission level PL, and the like. Here, because medical facilities such as hospitals frequently operate based on multiple shift schedules throughout a day (for example, a hospital with three shifts each staffed and supervised by different groups of employees), the access system 100 can utilize existing shift schedules, time clocks, and the like to recognize unusual user U access and/or requests. This configuration helps promote patient P safety by ensuring that users U are providing care in accordance with standard procedures and shift schedules.

By dynamically updating user U identification profiles IP via the identification module 108 over time, the access system 100 can effectively compensate for certain changes in user U appearance, performance, behavior, and the like. By way of illustration, where the access system 100 controls permission levels PL via the authorization module 106, and relies on identification data ID associated with facial recognition input data DI to differentiate between users U (such as with user sensors 98U realized as cameras), updating identification profiles IP in dossiers 112 with new facial imaging identification data ID at relatively short time intervals can help prevent misidentification that might otherwise occur when updating at longer intervals. Specifically, gradual changes in the user's U physical appearance over time (wrinkles, hair loss, and the like) are less noticeable when current identification data ID are compared against recently-updated identification profiles IP (for example, updated daily or weekly). Thus, the ability of the identification module 108 to update user U identification profiles IP with current identification data ID at a predetermined frequency allows the access system 100 to substantially mitigate misidentification that might otherwise occur when comparing current information data ID to outdated information data ID. Here, cooperation between the identification module 108 and the authorization module 106 helps to ensure that the user U is not misidentified and, thus, is not inadvertently restricted or prevented from accessing powered device 86 functions FN.

In some embodiments, the authorization module 106 relies on the most recently collected identification data ID in the identification profile IP of the user's U dossier 112 to identify the user U. However, it will be appreciated that input data DI can be stored in the dossier 112 for comparison across multiple data points and over extended periods of time, such as to facilitate observing and recording changes over time, identifying areas for improvement, and the like. Similarly, it will be appreciated that input data DI can be stored in the dossier 112 for comparison against different locations, different types and configurations of user interfaces 84 and/or powered devices 86, and the like. By way of non-limiting example, the input data DI can be used to compare one user's U performance in different environments or conditions, such as may be used to determine if the user U performs differently using the same powered device 86 in two different locations. Other configurations are contemplated.

As noted above, several different types of identification data ID can be updated by the identification module 108 to help identify and/or differentiate users U. In some embodiments, multiple types of identification data ID are stored in the dossier 112 and are respectively compared against current, observed identification data ID. This configuration can help prevent misidentification that might otherwise be caused by sudden changes in the user's U appearance, behavior, and the like.

Continuing with the previous example of facial recognition, it is conceivable that a user U with a clean-shaven face may be unrecognizable when compared against stored identification data ID depicting the user U with a full beard. Here, rather than immediately restricting or preventing user U access to one or more powered device 86 functions FN based on a sudden change in physical appearance like this, the access system 100 could be configured to simultaneously compare other types of current identification data ID against previously-recorded identification data ID stored in the user's U identification profile IP. For example, the identification module 108 could simultaneously monitor and compare input data DI associated with different types of identification data ID, such as voice recognition, walking/gait patterns, height, and the like, to prevent inadvertent misidentification caused by a sudden change in one particular type of identification data ID. Here in this example, the identification module 108 could note the sudden change to the user's U facial recognition data in the data reporter DR, and the access system 100 could be configured to subsequently identify or track that user U differently in response, such as by temporally ignoring outdated identification data ID which depict the user U with a full beard.

Figure 7:
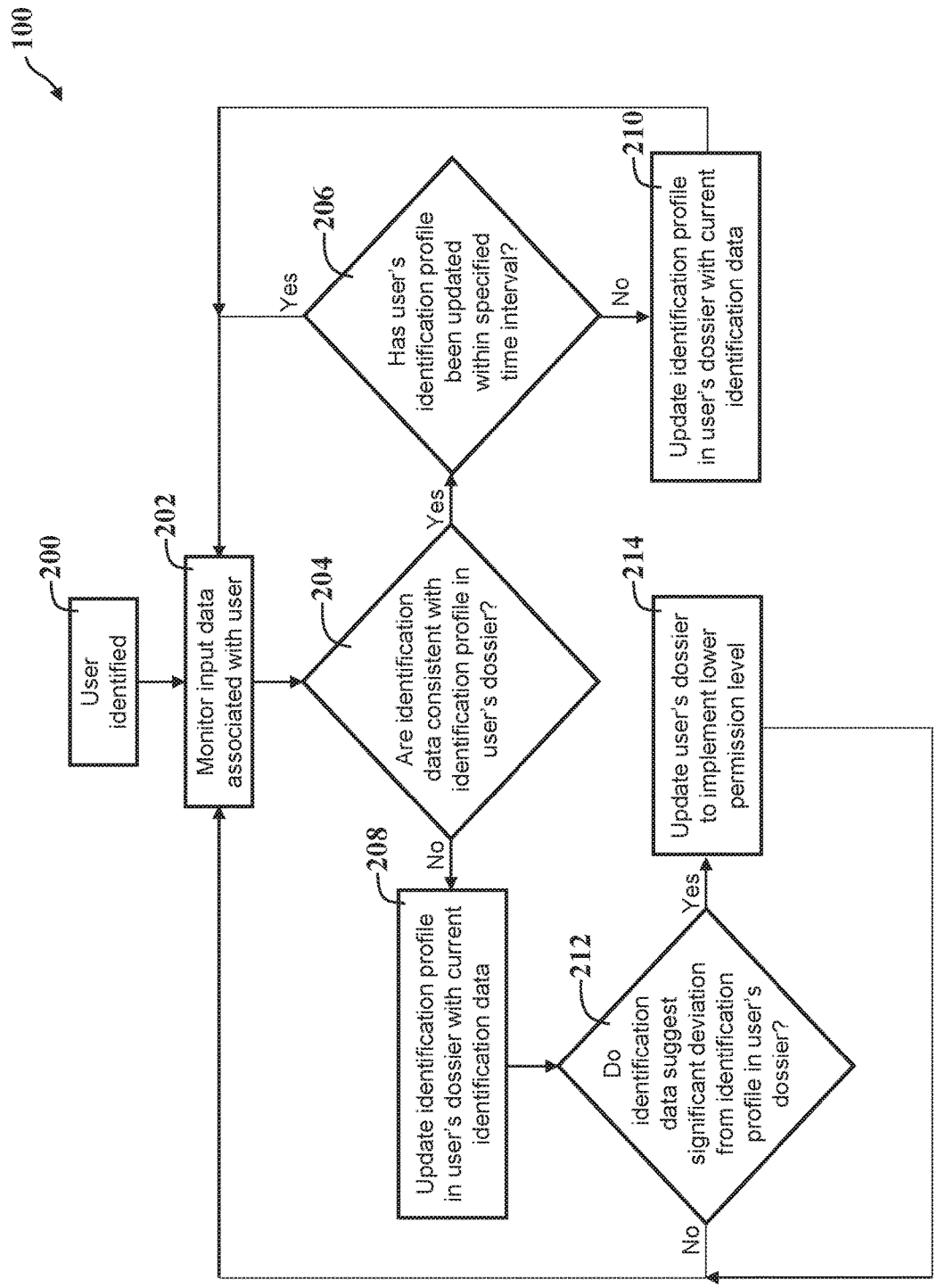
FIG. 7 is an exemplary logic map utilized by a patient support system according to one embodiment.

Referring now to FIG. 7, a logic map of one embodiment of the access system 100 is shown depicting cooperation between the authorization module 106 and the identification module 108. Specifically, FIG. 7 shows one embodiment of how user identification profiles IP can be updated by the identification module 108, and how significant deviations in identification data ID can be communicated to the authorization module 106 to restrict user U access to powered device 86 functions FN.

In FIG. 7, the access system 100 identifies the user U at block 200 and subsequently monitors input data DI associated with the user U via the input system 102 at block 202. Next, at block 204, the identification module 108 of the access system 100 compares current identification data ID associated with the user U against the identification profile IP stored in the user's U dossier 112. If the current identification data ID are consistent with the identification profile IP, the access system 100 moves to block 206, but if the current identification data ID are not consistent with the identification profile IP, or if the current identification data ID requires updates, the access system 100 moves to block 208, as described in greater detail below.

At block 206, the access system 100 checks to see if the user's U identification profile IP has been updated within a specified time interval. Here at block 206, the access system 100 can determine whether or not the user's U identification profile IP is outdated or otherwise should be updated. If the identification profile IP does not need updating, then the access system 100 returns to block 202. However, if updates are needed, the access system 100 moves to block 210 and updates the identification profile IP in the user's U dossier 112 with current identification data ID before returning to block 202. It will be appreciated that the need for updates, even where the identification data ID are considered to be consistent with the identification profile IP, can be determined in a number of different ways, such as based on a predetermined update schedule, based on certain changes in the user's U behavior, appearance, performance, and the like. In some embodiments, the access system 100 may determine the need to update the user's U identification profile IP based on changes occurring in the amount of time, processes, and the like which are required to properly identify the user U. By way of non-limiting example, minor changes in the user's U appearance, such as those caused by aging, may be consistent with the identification profile IP but may require increasing amounts of computing resources or multiple checks against other types of identification data ID to verify the user's U identity. Thus, updating the identification profile IP periodically and/or in response to these types of computing resource changes promotes improved subsequent identification speed. Other configurations are contemplated.

At block 208, where the access system 100 has previously determined the identification data ID are inconsistent with the identification profile IP in the user's U dossier 112, the access system 100 updates the identification profile IP in the user's U dossier 112 with current identification data ID before moving to block 212. Here at block 212, if the access system 100 determines that the current identification data ID are similar enough to the previous identification data ID in the identification profile IP, then the access system 100 returns to block 202. However, if the access system 100 determines that the current identification data ID suggest a significant deviation from the identification profile IP in the user's dossier 112, then the access system 100 moves to block 214 and updates user's U dossier 112 to implement a lower permission level PL before returning to block 202.

Those having ordinary skill in the art will appreciate that significant deviations from the user U identification profile IP can be predetermined (for example, set by a supervisor), or can be determined by the access system 100. Moreover, it will be appreciated that lowering the permission level PL for the user U based on deviations from the identification profile IP can be useful in a number of different situations. By way of illustration, if the user U has sustained injuries during an accident, they could have bruises, be wearing bandages, and/or may walk with a limp. Here, the identification module 108 could be configured to recognize that the user U has sustained an injury based on the changes in their physical appearance (bruises and bandages) and/or based on the changes in their behavior (walking slower than usual, with a limp). Based on the determination that the user U has been injured, the access system 100 could then lower the user's U permission level PL, whereby the authorization module 106 would then prevent the user U from accessing certain powered device 86 functions FN until they recover.

Here too, the access system 100 could update the data reporter DR in the user's U dossier 112 to note the injury and the adjusted permission level PL, which could be reviewed by a supervisor. It will be appreciated that, in some situations, no change of permission level PL may be necessary, and the access system 100 could update the data reporter DR in the user's U dossier 112 to note the injury and to update the identification profile IP for faster subsequent recognition of the user's U identification. Other configuration and scenarios are contemplated.

It is also conceivable that the access system 100 could lower the permission level PL for the user U based on deviations from the identification profile IP which are significant enough to question the user's U identity. By way of illustrative example, a user U returning from a two-week-long vacation stops by to visit his long-term patient P on his way home from the airport, but the user U has grown a beard, is wearing a hat and sunglasses, and is not dressed in scrubs. These deviations could conceivably be significant enough to cause the access system 100 to question the identity of the user U and subsequently limit or prevent the user U from accessing certain powered device 86 functions FN until the user's U identity is verified. For example, the access system 100 could communicate the discrepancy to a supervisor, or to another user U, via the data reporter DR for review and/or verification. Many other situations and configurations are contemplated.

Referring now to FIGS. 8-11, as noted above, in some embodiments, the access system 100 employs the authorization module 106 to modify the user's U permission level PL in certain situations to change the user's U ability to access powered device 86 functions FN, based such as on one or more of: changes in performance data ND associated with the user; changes in patient data PD associated with the patient P in that user's U care; and cooperation data CD between users U.

Figure 8:
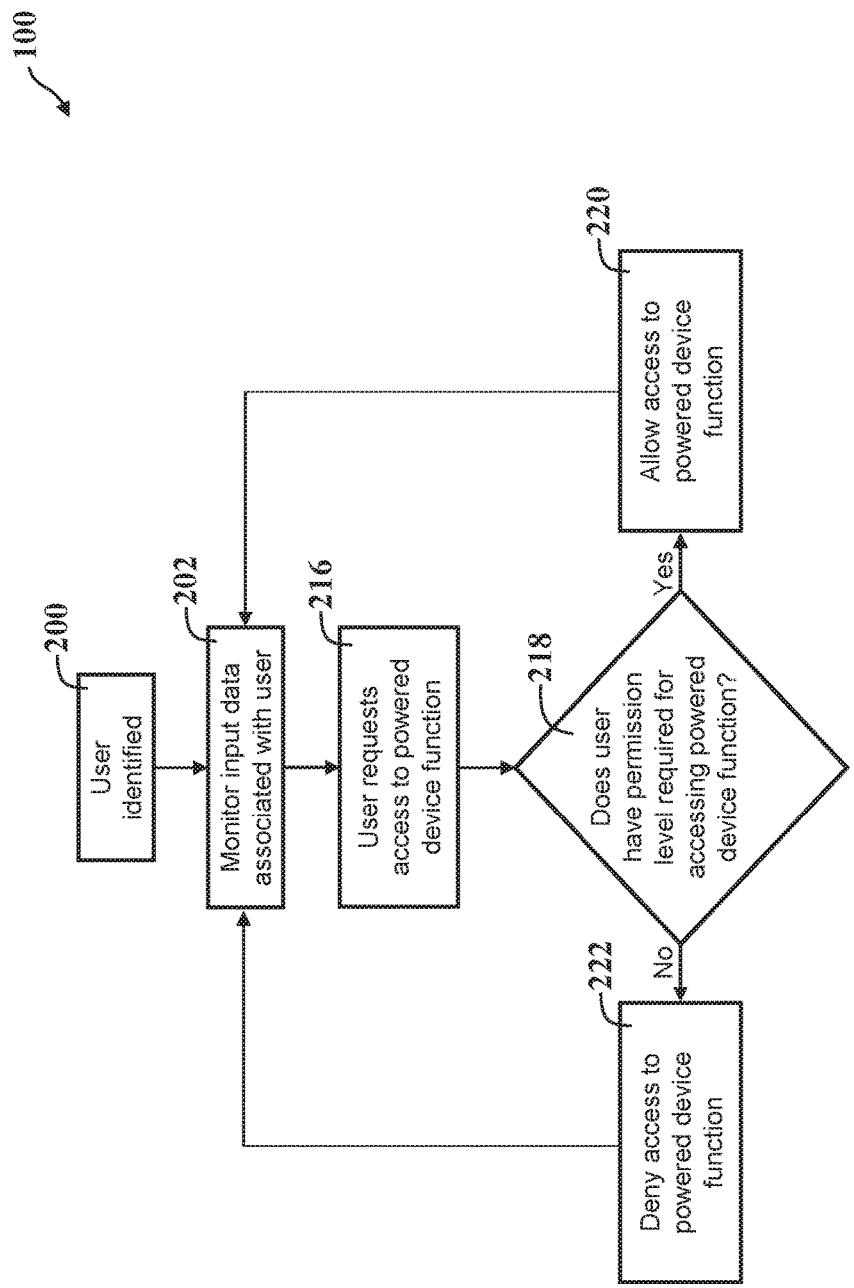
FIG. 8 is another exemplary logic map utilized by a patient support system according to one embodiment.

FIG. 8 depicts a logic map of one embodiment of the access system 100 to illustrate the general operation of the authorization module 106. Here too, the access system 100 identifies the user U at block 200 and subsequently monitors input data DI associated with the user U via the input system 102 at block 202. Next, at block 216, the user U requests access to a specific powered device 86 function FN, such as by approaching or engaging a user interface 84. In response to the user's U request, at block 218, the authorization module 106 checks to see if the user U has the permission level PL required for accessing the requested powered device 86 function FN. If the user U has the requisite permission level PL, the authorization module 106 moves from block 218 to block 220 and allows access to the powered device 86 function FN before returning to block 202. Conversely, if the user U does not have the requisite permission level PL, then the authorization module 106 moves from block 218 to block 220 and denies access to the powered device 86 function FN before returning to block 202.

In order to implement changes in user U access to powered device 86 functions FN, the access system 100 can be configured to alter the permission level PL of the user U, and/or to alter the required permission level PL of the powered device 86. As noted above, permission levels PL can be defined, assigned, or changed in a number of different ways. In general, it will be appreciated that certain powered devices 86 and/or functions FN may require different permission levels PL than other powered devices 86 and/or functions FN. Further, while certain powered devices 86 may require a common permission level PL associated with all functions FN the powered device 86 is able to perform, other powered devices 86 may require different permission levels PL for different functions FN. Thus, it will be appreciated that users U could have different permission levels PL stored in their dossier 112 for every function FN available within the access system 100.

In some embodiments, the access system 100 can restrict access to powered device 86 functions FN by modifying its required permission level PL based on changes in the location, status, and the like, of the powered device 86 itself, the patient P, and/or the user U. By way of illustration, a powered device 86 may require different permission levels PL based on whether or not the powered device 86 is located within a sterile field. Similarly, a malfunctioning powered device 86 can be "locked out" by modifying its required permission level PL to deny access to regular users U but allow access to repair technicians, prevent all access when patients P are nearby, and the like.

As noted above, the access system 100 can restrict access to powered device 86 functions FN by changing the user's U permission level PL. In one embodiment, the permission level PL comprises one of a first permission level PL1 that restricts the user U from operating the powered device 86 with the input system 102 to perform the function FN, and a second permission level PL2 that authorizes the user U to operate the powered device 86 with the input system 102 to perform the function FN. In other embodiments, such as where the powered device 86 can perform multiple functions FN, the second permission level PL2 authorizes the user U to operate the powered device 86 with the input system 102 to perform a first function FN1, and a third permission level PL3 authorizes the user to operate the powered device 86 with the input system 102 to additionally perform a second function FN2.

In the illustrative example noted above and described in greater detail below, the permission levels PL are configured in an escalated manner such that accessing the first function FN1 requires the user U to have a permission level PL greater than the first permission level PL1, and accessing the second function FN2 requires the user U to have a permission level PL greater than the second permission level PL2. Other, non-escalated configurations are contemplated. For example, rather than denoting escalated permission levels PL, the terms "first permission level PL1," "second permission level PL2," "third permission level PL3," and the like, could be used as unique identifiers or labels merely to differentiate between different functions FN and/or powered devices 86.

In some embodiments, the authorization module 106 is configured to switch the permission level PL of the user U from the second permission level PL2 or the third permission level PL3 to the first permission level PL1 in the event that performance data ND fails to meet a predetermined performance criterion. Put differently, poor user U performance can result in limited access to certain powered device 86 functions FN. By way of illustrative example, if the user U forgets to "plug in" a battery-operated, chargeable powered device 86 after use, the access system 100 may subsequently lower the user's U permission level PL for that powered device 86 to disable the user's U access to help ensure that other users U are not routinely unable to use the powered device 86 because of dead batteries. Conversely, in some embodiments, the authorization module 106 is configured to switch the permission level PL of the user U from the second permission level PL2 to the third permission level PL3 in the event that performance data ND exceeds a predetermined performance criterion. Here, by way of illustrative example, if the user U becomes proficient with a powered devices 86 that can perform additional functions FN with escalated permission level PL requirements, then the access system 100 may allow that user U to access certain additional functions FN based on their proficiency. Thus, the authorization module 106 can be configured to adjust the user's U permission level PL based on performance data ND for any function FN of any powered device 86.

Figure 9:
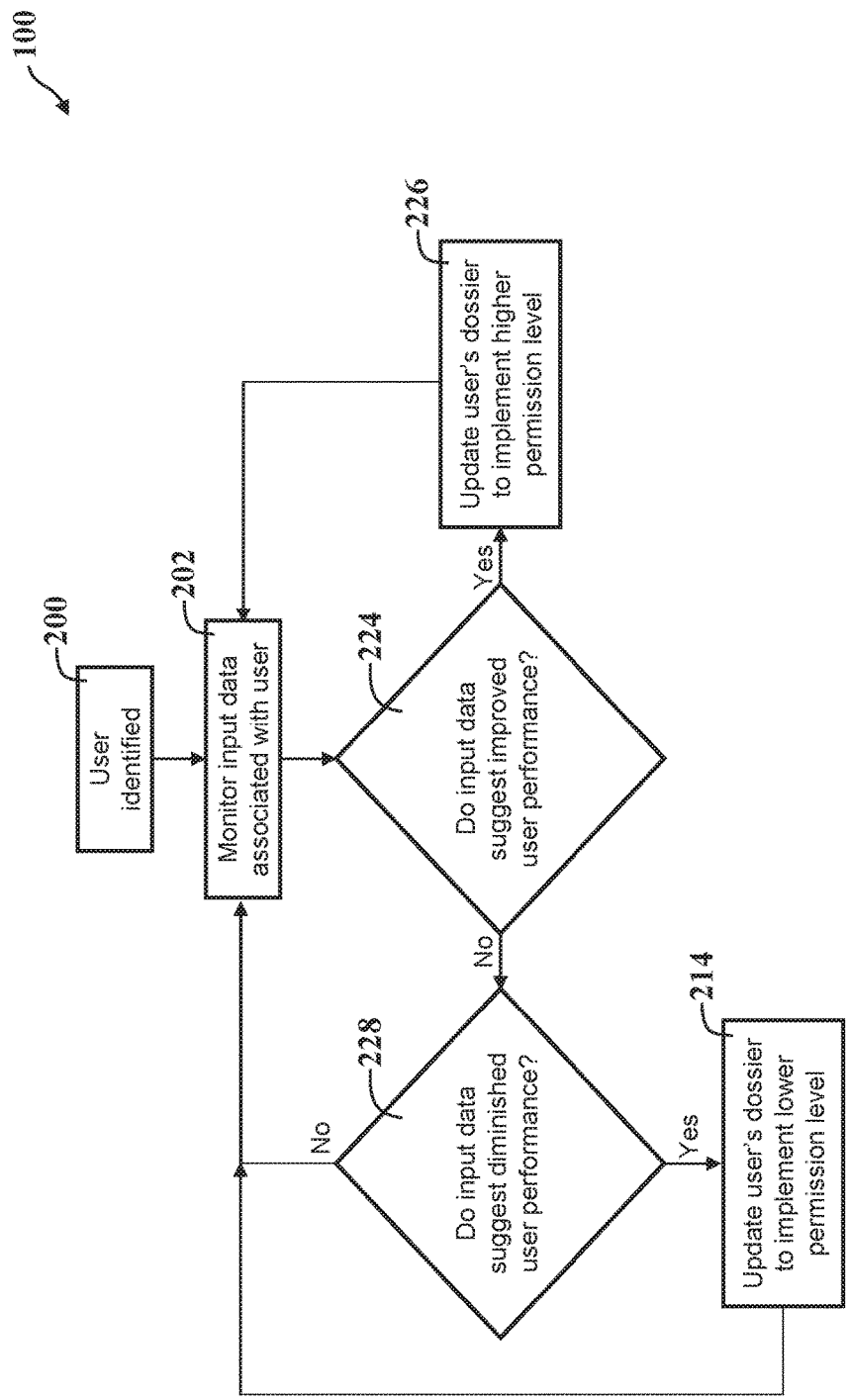
FIG. 9 is another exemplary logic map utilized by a patient support system according to one embodiment.

FIG. 9 depicts a logic map of one embodiment of the access system 100 to illustrate how the authorization module 106 can use performance data ND to adjust the user's U permission level PL. Here too, the access system 100 identifies the user U at block 200 and subsequently monitors input data DI associated with the user U via the input system 102 at block 202. Next, at block 224, the authorization module 106 reviews certain input data DI, such as performance data ND, to evaluate the user's U performance. If the input data DI suggest improved user U performance, the authorization module 106 moves to block 226 and updates the user's U dossier 112 to implement a higher permission level PL before subsequently returning to block 202. Conversely, if the input data DI do not suggest improved user U performance, the authorization module 106 moves to block 228. Here, at block 228, if the input data DI suggest that user U performance is generally normal, the authorization module 106 returns to block 202. However, if the input data DI suggest diminished user U performance, the authorization module 106 moves to block 214 and updates the user's U dossier 112 to implement a lower permission level PL before subsequently returning to block 202.

As noted above, the access system 100 can use the input system 102 to monitor input data DI associated with the user U and also input data DI associated with the patient P in the user's U care. In some embodiments, the authorization module 106 is configured to modify the permission level PL of the user U based on patient data PD associated with the patient P. By way of illustrative example, if a new and less-experienced user U is providing care for a patient P whose health or status begins to deteriorate significantly, the access system 100 could limit this less-experienced user's U access to certain powered devices 86 used in connection with providing care to the patient P until the patient's P health or status improves, is verified by a more-experienced user U, and the like. By way of further illustrative example, if the access system 100 determines that a patient P is reacting poorly to intravenous pain medication supplied via a pump, the authorization module 106 could prevent certain users U, such as floor nurses, from increasing the pump's flowrate until an appropriately trained user U, such as a doctor, can assess the patient's P condition further.

Figure 10:
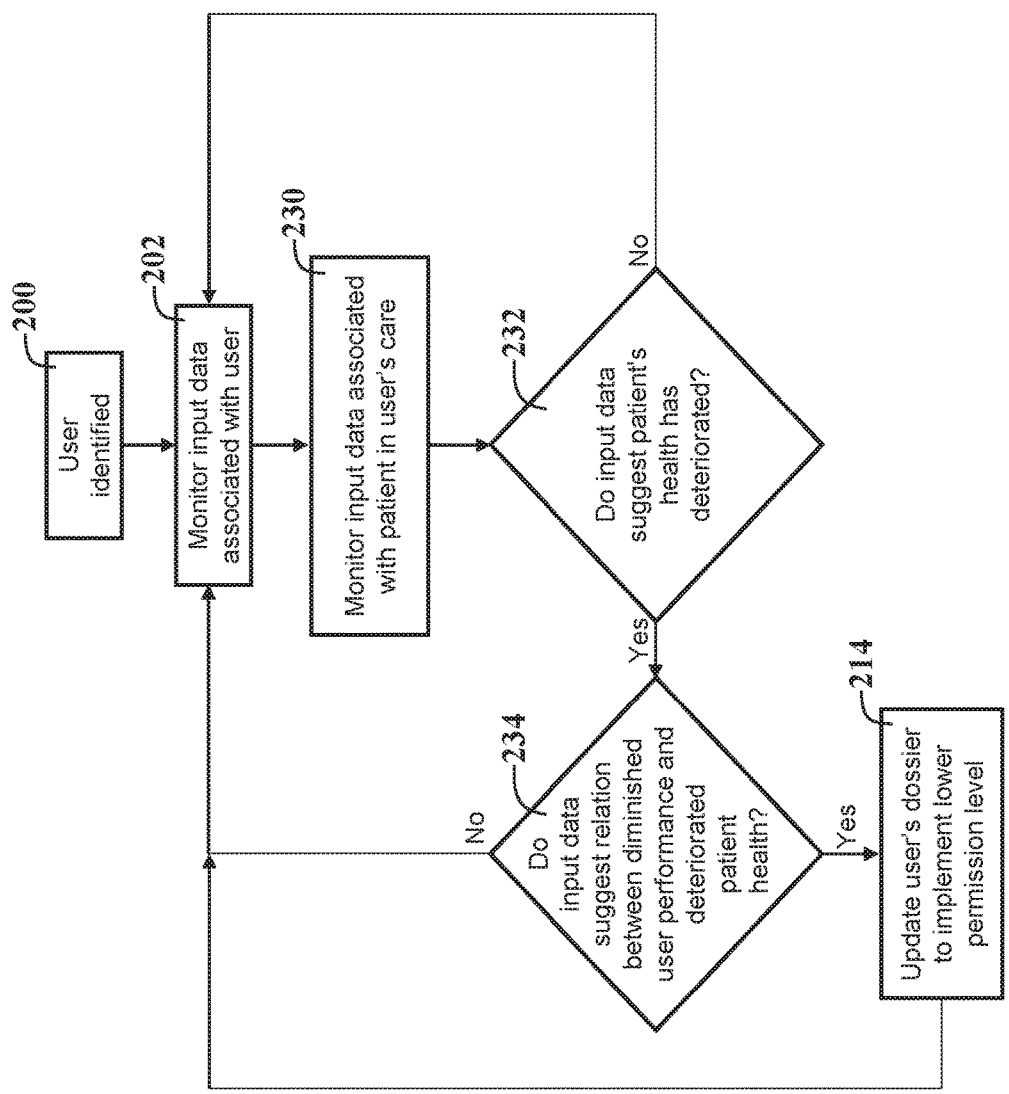
FIG. 10 is another exemplary logic map utilized by a patient support system according to one embodiment.

FIG. 10 depicts a logic map of one embodiment of the access system 100 to illustrate how the authorization module 106 can use performance data ND and patient data PD to adjust the user's U permission level PL. Here too, the access system 100 identifies the user U at block 200 and subsequently monitors input data DI associated with the user U via the input system 102 at block 202. Next, at block 230, the authorization module 106 monitors input data DI associated with the patient P via the input system 102 and, at block 232, determines whether patient data PD suggest that the patient's P health has deteriorated. Here, if there are no changes to the patient's health, status, condition, and the like, the authorization module returns to block 202. However, if the patient's health, status, condition, and the like, has deteriorated, then the authorization module moves to block 234 to determine if there have been changes in any other input data DI, such as performance data ND, that suggest a relation/correlation between deteriorated patient P health and user U performance. Here, if the input data DI suggest nothing to indicate that the patient P's condition worsened as a result of the user's U performance, then the authorization module 106 returns to block 202. However, if the input data DI suggest a relation between diminished user U performance and deteriorated patient P health, then the authorization module 106 moves to block 214 and updates the user's U dossier 112 to implement a lower permission level PL before subsequently returning to block 202.

As noted above, the access system 100 can use the input system 102 to monitor input data DI associated with multiple users U, and can adjust the permission levels PL of different users U independently. Moreover, the authorization module 106 can modify permission levels PL of one or more users U based on cooperation data CD, as noted above and as is described in greater detail below.

In one embodiment, care is provided to the patient P by a first user U1 and by a second user U2. Each of the users U1, U2 has a respective permission level PL which dictates whether that user U1, U2 has permission to operate certain powered devices 86 with the input system 102 to perform certain functions FN, as described above. Here, the authorization module 106 determines cooperation data CD for the users U1, U2 relating to cooperation between those users U1, U2 in providing care to the patient P. Based on these cooperation data CD, the authorization module 106 can modify the permission level PL of at least one user U1, U2.

It will be appreciated that cooperation data CD between users U1, U2 can relate to a number of different types of input data DI. In one embodiment, the cooperation data CD relate to the proximity of the first user U1 and the second user U2 to the patient support apparatus 30. In one embodiment, the cooperation data CD relate to the proximity of the first user U1 and the second user U2 to the patient P. In one embodiment, the cooperation data CD relate to the proximity of the first user U1 to the second user U2. In one embodiment, the cooperation data CD relate to communications between the first user U1 and the second user U2. It will be appreciated that cooperation data CD can relate to a number of different types of input data DI, and can be used to effect modification of user U permission levels PL in different ways. Specifically, those having ordinary skill in the art will appreciate that communication can be based on things other than proximity and direct, in-person interaction between users U1, U2. For example, communications could occur across audio and/or video-based systems such as telephony, video conferencing, and the like. Furthermore, communications could be based on or otherwise involve authorization, such as electronic or written authorization, from one user U1 granting another user U2 a permission level PL modification. Specifically, as will be appreciated from the subsequent description of the access system 100 below, "communications" could include any suitable type interaction between/among more than one user U1, U2 that sufficient to give or adjust permission to one or more users U. By way of non-limiting example, "communications" could occur through video conferencing, telephone, email, handwritten message, voice message, video message (with or without voice), gesture confirmation, and the like. Thus, one of the users U1 does not necessarily have to be physically present and next to the other user U2 in order to obtain access to the first user to operate certain powered devices 86 with the input system 102 to perform certain functions FN, as described above. It will be appreciated that different types of communications could be used to effect temporary changes in permission level PL, depending on the configuration of the access system 100 and the specific cooperation data CD observed.

As noted above, the access system 100 could utilize in-person communications between users U1, U2 in a number of different ways. By way of illustration, it is conceivable that both the first user U1 and the second user U2 could have respective permission levels PL which prevent them from individually accessing powered devices 86 necessary to transfer the patient P occupying the patient support apparatus 30 off of the patient support deck 38, such as where the weight of the patient P is greater than either of the users U1, U2 could manage on their own. However, cooperation data CD between the users U1, U2 may indicate that the first user U1 and the second user U2, working together, could safely transfer the patient P. Based on this cooperation data CD, the access system 100 could modify one or both of the users' U1, U2 permission levels PL to allow access to powered device 86 functions FN associated with facilitating patient P transfer.

By way of further illustration, it is conceivable that the first user U1 could have a low permission level PL that is insufficient to access a particular powered device 86 function FN, and the second user U1 could have a higher permission level PL that is sufficient to access the function FN. For example, the first user U1 may be a nurse who is not authorized to use a computer system 86 to access patient records FN, and the second user U2 could be a doctor who is authorized to access patient records FN. Here in this example, the authorization module 106 could use cooperation data CD, such as input data ID indicating that both the nurse U1 and the doctor U2 are in the same room and are working closely together to provide care to the patient P, to temporarily modify the nurse's U1 permission level PL to allow access to patient records FN while the doctor U2 is nearby without necessitating that the doctor U2 actually operate the computer system 86. As noted above, it will be appreciated that cooperation data CD can be used by the authorization module 106 based on a number of different types of communication, including audio, voice, written, and/or electronic communication.

Figure 11:
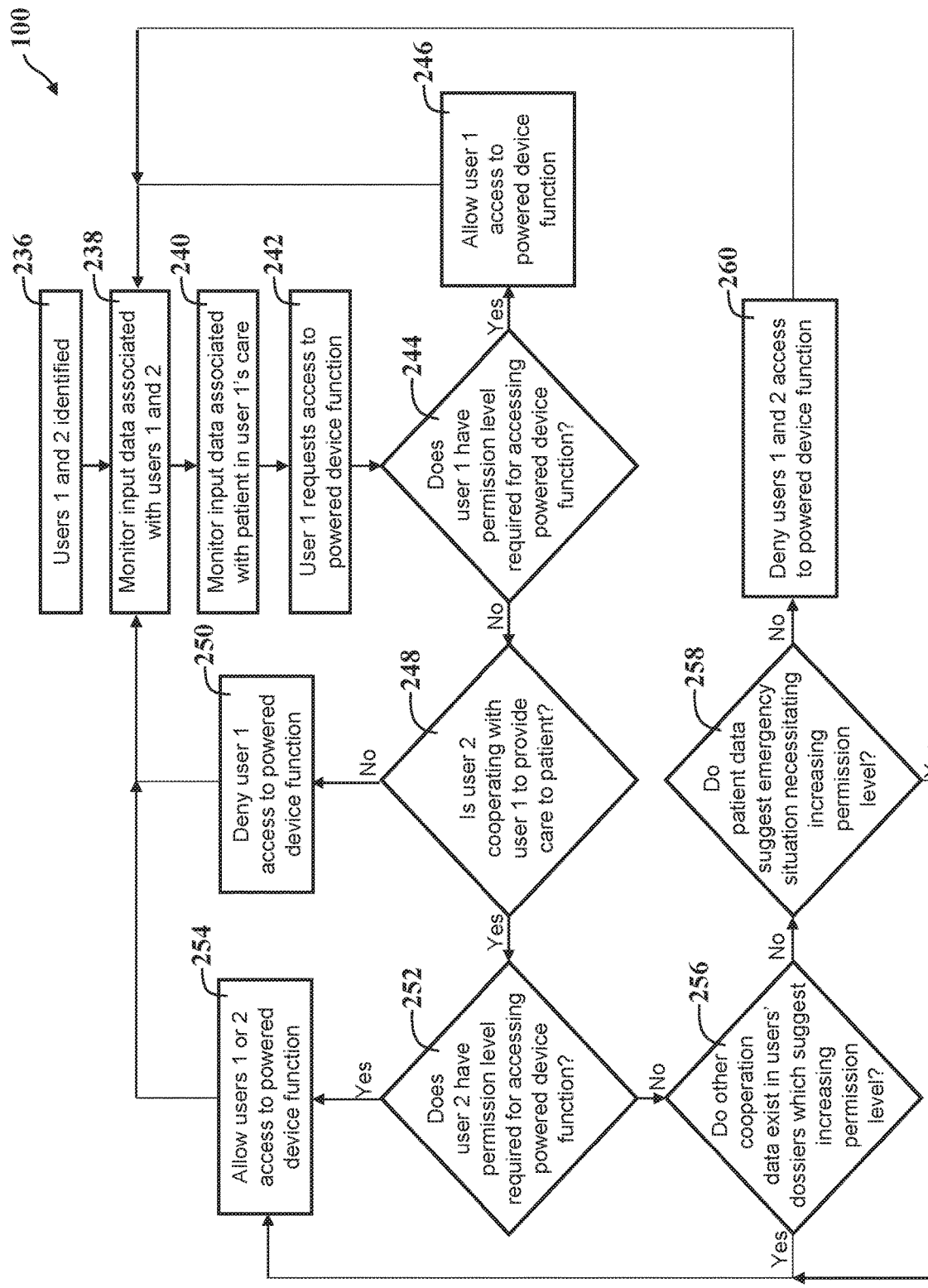
FIG. 11 is another exemplary logic map utilized by a patient support system according to one embodiment.

FIG. 11 depicts a logic map of one embodiment of the access system 100 to illustrate how the authorization module 106 can use cooperation data CD between first and second users U1, U2 that cooperate to provide care to the patient P. In this example, the access system 100 identifies the users U1, U2 at block 236 and subsequently monitors input data DI associated with the users U1, U2 via the input system 102 at block 238. Next, at block 240, the authorization module 106 monitors input data DI associated with the patient P in the first user's U1 care via the input system 102. Next, at block 242, the first user U1 requests access to a specific powered device 86 function FN. In response to the first user's U1 request, at block 244, the authorization module 106 checks to see if the first user U1 has the permission level PL required for accessing the requested powered device 86 function FN. If the first user U1 has the requisite permission level PL, the authorization module 106 moves from block 244 to block 246 and allows the first user U1 to access to the powered device 86 function FN before returning to block 238. However, if the first user U1 does not have the requisite permission level PL, then the authorization module 106 moves from block 244 to block 248 to check for input data DI associated with cooperation data CD between the first user U1 and the second user U2.

At block 248, the authorization module 106 confirms that the second user U2 is cooperating with the first user U1 to provide care to the patient P, such as by input data DI which indicates both users U1, U2 are nearby the patient P. If the second user U2 is not cooperating with the first user U1, then the authorization module 106 moves to block 250 and denies the first user U1 access to the powered device 86 function FN. However, if the second user U2 is cooperating with the first user U1, then the authorization module 106 moves to block 252 and checks to see if the second user U2 has the permission level PL required for accessing the requested powered device 86 function FN.

At block 252, if the second user U2 has the requisite permission level PL, the authorization module 106 moves from block 252 to block 254 and allows the first user U1 and/or the second user U2 access to the powered device 86 function FN before returning to block 238. However, if the second user U2 does not have the requisite permission level PL, then the authorization module 106 moves from block 252 to block 256.

At block 256, the authorization module 106 checks for other cooperation data CD in the users' U1, U2 dossiers 112, as well as additional input data DI, which suggest temporarily increasing one or both of the users' U1, U2 permission level PL to allow access to the powered device 86 function FN. If the cooperation data CD do suggest increasing the permission level PL, then the authorization module 106 moves to block 254 and allows the first user U1 and/or the second user U2 access to the powered device 86 function FN before returning to block 238. However, if the cooperation data CD do not suggest increasing the permission level PL, then the authorization module 106 moves to block 258.

At block 258, the authorization module checks for patient data PD which indicate an emergency situation necessitating or otherwise warranting increasing the permission level PL of one or both users U1, U2. Here, for example, even where both users U1, U2 have permission levels PL insufficient to access adjusting the vertical configuration 38A, 38B of the patient support deck 38, and even where no cooperation data CD between the users U1, U2 exist that merits adjusting the permission level PL, the authorization system 100 could nevertheless allow the users U1, U2 to lower the patient support deck 38 during an emergency, such as where the patient P is having a heart attack and needs immediate cardiopulmonary resuscitation (CPR). However, if at block 258 the access system 100 determines no emergency situation is present, then the authorization module 106 moves to block 260 and denies both users U1, U2 access to the powered device 86 function FN before returning to block 238.

In this way, the embodiments of the access system 100 and patient support apparatus 30 of the present disclosure afford significant opportunities for enhancing the functionality and operation of powered devices 86 by managing users U and dynamically controlling access to powered devices 86 by specific users U and/or patients P in a number of different situations. Moreover, the access system 100 allows users U and patients P to be monitored and tracked dynamically, in a number of different ways, and based on a number of different types of input data DI, to ensure and maintain proper user U identification and access while, at the same time, preventing unauthorized access to powered devices 86.

As noted above, the subject patent application is related to U.S. Provisional Patent Application No. 62/525,377 filed on Jun. 27, 2017. In addition, the subject patent application is also related to: U.S. Provisional Patent Application No. 62/525,353 filed on Jun. 27, 2017 and its corresponding Non-Provisional patent application Ser. No. 16/020,068 filed on Jun. 27, 2018; U.S. Provisional Patent Application No. 62/525,359 filed on Jun. 27, 2017 and its corresponding Non-Provisional patent application Ser. No. 16/020,052 filed on Jun. 27, 2018; U.S. Provisional Patent Application No. 62/525,363 filed on Jun. 27, 2017 and its corresponding Non-Provisional patent application Ser. No. 16/020,085 filed on Jun. 27, 2018; U.S. Provisional Patent Application No. 62/525,368 filed on Jun. 27, 2017 and its corresponding Non-Provisional patent application Ser. No. 16/019,973 filed on Jun. 27, 2018; and U.S. Provisional Patent Application No. 62/525,373 filed on Jun. 27, 2017 and its corresponding Non-Provisional patent application Ser. No. 16/020,003 filed on Jun. 27, 2018. The disclosures of each of the above-identified Provisional Patent Applications and corresponding Non-Provisional Patent Applications are each hereby incorporated by reference in their entirety.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

What is claimed is:

1. An access system for managing users engaged in providing care to patients, said access system comprising:
   a patient support apparatus comprising a frame, a patient support surface configured to support the patient, and a powered device having a function;
   an input system in communication with said powered device and configured to receive input data; and
   a user control system in communication with said input system, said user control system comprising an authorization module configured to: access a permission level for each of a first user and a second user, said permission levels dictating whether the users have permission to operate said powered device with said input system to perform said function; determine cooperation data relating to cooperation of the first user and the second user in providing care for the patient; and modify said permission level of at least one of the first user and the second user based on said cooperation data in response to both the first user and second user being within a predetermined proximity of said patient support apparatus.

2. The access system as set forth in claim 1, wherein said permission level for the first user comprises a first permission level that restricts the first user from operating said powered device with said input system to perform said function;
   wherein said permission level for the second user comprises a second permission level that authorizes the second user to operate said powered device with said input system to perform said function; and
   wherein said authorization module is configured to switch said permission level for the first user from said first permission level based on said second permission level based on said cooperation data in response to both the first user and second user being within the predetermined proximity of said patient support apparatus.

3. The access system as set forth in claim 1, wherein said input system comprises one or more of a user interface and a sensor.

4. The access system as set forth in claim 1, wherein said input system comprises a portable electronic device carried by a user of said access system.

5. The access system as set forth in claim 1, wherein said authorization module is configured to modify one or more of said permission levels based on data associated with the user.

6. The access system as set forth in claim 1, wherein said authorization module is configured to modify one or more of said permission levels based on patient data associated with the patient.

7. The access system as set forth in claim 1, wherein said user control system comprises an identification module configured to: access identification profiles associated with users; receive identification data relating to the users of the patient support apparatus; and update said identification profiles based on said identification data.

8. An access system for managing users engaged in providing care to patients, said access system comprising:
   a patient support apparatus comprising a frame, a patient support surface configured to support the patient, and a powered device having a function;
   an input system in communication with said powered device and configured to receive input data; and
   a user control system in communication with said input system, said user control system comprising an authorization module configured to:
   access a permission level for each of a first user and a second user, said permission levels dictating whether the users have permission to operate said powered device with said input system to perform said function, wherein said permission level for the first user comprises a first permission level that restricts the first user from operating said powered device with said input system to perform said function, and wherein said permission level for the second user comprises a second permission level that authorizes the second user to operate said powered device with said input system to perform said function;
   determine cooperation data relating to cooperation of the first user and the second user in providing care for the patient; and
   switch said permission level for the first user from said first permission level to said second permission level based on said cooperation data in response to both the first user and second user being within a predetermined proximity of said patient support apparatus.

9. The access system as set forth in claim 8, wherein said input system comprises one or more of a user interface and a sensor.

10. The access system as set forth in claim 8, wherein said input system comprises a portable electronic device carried by a user of said access system.

11. The access system as set forth in claim 8, wherein said authorization module is configured to modify one or more of said permission levels based on data associated with the user.

12. The access system as set forth in claim 8, wherein said authorization module is configured to modify one or more of said permission levels based on patient data associated with the patient.

13. The access system as set forth in claim 8, wherein said user control system comprises an identification module configured to: access identification profiles associated with users; receive identification data relating to the users of the patient support apparatus; and update said identification profiles based on said identification data.

* * * * *